(12) United States Patent
Johnston et al.

(10) Patent No.: US 6,752,995 B2
(45) Date of Patent: Jun. 22, 2004

(54) NUCLEIC ACID AND POLYPEPTIDE SEQUENCES USEFUL AS ADJUVANTS

(75) Inventors: Stephen A. Johnston, Dallas, TX (US); Michael J. McGuire, Irving, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 10/123,058

(22) Filed: Apr. 15, 2002

(65) Prior Publication Data

US 2003/0194695 A1 Oct. 16, 2003

(51) Int. Cl.$^7$ .............................................. A61K 45/00
(52) U.S. Cl. ............................... 424/278.1; 424/232.1; 514/44
(58) Field of Search ........................... 424/278.1, 232.1, 424/186.1, 237.1; 514/44, 2, 12; 536/23.72; 435/320.1

(56) References Cited

U.S. PATENT DOCUMENTS

| | | | |
|---|---|---|---|
| 6,365,393 B1 * | 4/2002 | Schmeer et al. | 435/235.1 |
| 2002/0076418 A1 | 6/2002 | Hirth-Dietrich et al. | 424/232.1 |
| 2003/0013706 A1 * | 1/2003 | Robinson et al. | 435/5 |
| 2003/0109483 A1 * | 6/2003 | Cassell et al. | 514/44 |

FOREIGN PATENT DOCUMENTS

WO 95/22978 * 8/1995 ........... A61K/35/76

OTHER PUBLICATIONS

Moss, B. Poxviridae: The Viruses and Their Replication. In Fields Virology, 3rd edition, ed. B.N. Fields et al, Lipincott-Raven Publishers, Philadelphia, 1996. Pp. 2537–2671.*

Parkin et al. An Overview of the immune system. The Lancet 357:177–1789, Jun. 2, 2001.*

Sullivan et al. Virology 202:968–973, 1994.*

Diven, "An overview of poxviruses," *J. Am Acad Dermatol.*, 44(1):1–16, 2001.

Johannessen et al., "Human Orf," *J. Cutan. Pathol.*, 2:265–283, 1975.

McKeever et al., "Studies of the pathogenesis of Orf virus infection in sheep," *J. Comp. Path.*, 99:317–328, 1988.

* cited by examiner

Primary Examiner—Mary E. Mosher
(74) Attorney, Agent, or Firm—Richard Aron Osman

(57) ABSTRACT

In the present invention parapox genomes were screened using a novel expression strategy to test genes for dendritic cell recruitment activity. One gene was identified, designated as B2WL, that induces dendritic cell accumulation when expressed in skin. In additional testing a second gene, PP30, was identified that exhibited adjuvant activity in the absence of stimulating dendritic cell accumulation at the site of inoculation. When co-inoculated with an antigen-encoding plasmid, both genes acted as adjuvants in stimulating an antibody response to antigens. Furthermore, nucleic acids encoding the identified B2WL peptide adjuvant enhanced the level of protection against viral infection provided by immunization with an HA-expression plasmid. Thus, novel adjuvants for genetic immunization are identified. The invention also demonstrates the application of the linear expression element (LEE) technology for screening genomes of pathogens that may contain genes that are useful when expressed and tested in a novel context.

26 Claims, 4 Drawing Sheets

NUCLEIC ACID AND POLYPEPTIDE SEQUENCES USEFUL AS ADJUVANTS

The government owns partial rights in the present invention pursuant to grant number N652369915426, Account number 36001 from DARPA.

BACKGROUND OF THE INVENTION

1. Field of the Invention

The present invention relates generally to the fields of immunopreventive therapy and vaccine development. More particularly, it concerns the development of novel polypeptides and nucleic acids encoding such polypeptides that can be used to initiate, stimulate, and/or enhance an immune response. These polypeptides and nucleic acids encoding them can be used as adjuvants that can be used to generate more potent and robust vaccines against desired polypeptides. Additionally, these polypeptides and nucleic acids can be used to initiate or enhance an innate immune response in a subject.

The application also describes the use of dendritic cell recruitment using a novel strategy.

2. Description of Related Art

Many methodologies of medical treatment can be envisioned that will require or benefit from an ability to initiate, stimulate, and/or enhance an immune response. These methodologies include those depending upon the creation of an immune response against a desired antigenic polypeptide and those that depend upon the initiation or modulation of an innate immune response.

The use of adjuvants for immunization are well known in the art however, the challenge of developing safe and effective adjuvants is ongoing. A primary disadvantage with current adjuvants is that most are unsuitable for use in human vaccines, including especially genetic vaccines.

One of the first adjuvant developed was Freund's complete adjuvant. This adjuvant has excellent immunopotentiating properties, however, its side effects are so severe that it renders the use of this adjuvant unacceptable in humans, and sometimes in animals. Other oil emulsions adjuvants such as Incomplete Freund's Adjuvant (IFA); Montanide ISA (incomplete seppic adjuvant); Ribi Adjuvant System (RAS); TiterMax; and Syntex Adjuvant Formulation (SAF) are also associated with various side effects such as toxicity and inflammation. Oil based adjuvants in general are less desirable in genetic immunization; they create side effects such as visceral adhesions and melanized granuloma formations, and they cannot form a homogeneous mixture with DNA preparations such as DNA-based vaccines.

Bacterially derived adjuvants, such as MDP and lipid A are also associated with undesirable side effects. Bacterial products such as *Bordetella pertussis, Corynebacterium granulosum* derived P40 component, Lipopolysaccharide (LPS), Mycobacterium and its components, and *Cholera toxin*, are another preferred group of adjuvants however, although they may augment the immune response to other antigens they are associated with side effects such as epilepsy as in the case of *B. pertussis*, and varying levels of toxicity.

Mineral compounds which include aluminum phosphate or aluminum hydroxide (alum) and calcium phosphate as adjuvants may also be employed. Aluminum salt-based adjuvants (such as alum) have excellent safety records but poor efficacy with some antigens (Sjolander et al., 1998). They are the most frequently used adjuvants for vaccine antigen delivery presently. Aluminum salt-based adjuvants are generally weaker adjuvants than emulsion adjuvants. The most widely used is the antigen solution mixed form with pre-formed aluminum phosphate or aluminum hydroxide however, these vaccines are difficult to manufacture in a physico-chemically reproducible way which results in batch to batch variation of the vaccine. When used in large quantity an inflammatory reaction may occur at the site of injection which is generally resolved in a few week although chronic granulomas may occasionally form.

Other available adjuvants, are know to those skilled in the art. One such adjuvant include liposomes. Although liposomes show favorable characteristics for use in bulk vaccine preparations, the preparation proves to be rather complex for use with occasional antigens prepared for injection especially when the antigen is available in limited quantity. Gerbu$^R$ adjuvant, an aqueous phase adjuvant although associated with minimal inflammatory effects may require frequent boosting to maintain high titer. Squalene also included in the group of adjuvants have been associated with the Gulf War Syndrome and include such side effects as arthritis, fibromayalgia, rashes, chronic headaches, sclerosis and non healing skin lesions to name a few.

Various polysaccharide adjuvants are also known to those skilled in the art. For example, Yin et al., (1989) describe the use of various pneumococcal polysaccharide adjuvants on the antibody responses of mice. The doses that produce optimal responses, or that otherwise do not produce suppression, as indicated in Yin et al., (1989) should be employed. Polyamine varieties of polysaccharides are particularly preferred, such as chitin and chitosan, including deacetylated chitin.

One approach to circumvent the challenges of adjuvants entails the pox viruses. Pox viruses belong to a diverse family of viruses that can affect both humans and animals. Parapoxviruses are one member of this family that is known to affect humans, and is of special interest dermatologically since they are epitheliotropic (Diven, 2001). *Parapoxvirus ovis* is a 150 kb double-stranded DNA virus that causes skin pock lesions in susceptible animals. Transmittance of this viral infection, though mainly affecting sheep and cattle, can occur in human handling infected animals (Johannessen et al, 1975). The infection begins at a break in the skin or inflamed hair follicle and is completely resolved in 4–6 weeks though generally no specific immune response is induced. Therefore, the caveat of this viral infection is that the animal or individual can be re-infected with no enhancement of resolution of the individual lesions in subsequent infections (McKeever et al, 1988). Furthermore, specific immunity to parapox is not acquired and proves to be a challenge since no parapox-based vaccine is available.

Live vaccines can be problematic in their own way, however. Even they can fail to shield against some diseases. Those that work can cause full-blown illness in people whose immune system is compromised, as in cancer patients undergoing chemotherapy, AIDS sufferers and the elderly. Such individuals may also contract disease from healthy people who have been inoculated recently. Moreover, weakened viruses can at times mutate in ways that restore virulence, as has happened in some monkeys given an attenuated simian form of HIV, the virus that causes AIDS. For some diseases, the risks of reversion to virulence are intolerable.

Hence, more effective adjuvants are needed that will enhance the immune response induced by gene vaccines. In order to develop such strategies there is a need to identify factors that are directly able to interact with the immune system as in the natural viral infection of parapox, thereby allowing for the identification of potential new adjuvants for genetic immunization.

SUMMARY OF THE INVENTION

The present invention overcomes the deficiencies in the art by identifying polypeptides that are useful in modulating immune responses and nucleic acid sequences that encode such polypeptides. For example, the applicants have identified specific parapox genetic sequences that can be employed in these manners.

In general embodiments the present invention provides a method of stimulating the immune system of a subject, comprising introducing an immunostimulatory polypeptide from Parapox virus into the subject. In a preferred embodiment, the polypeptide is a polypeptide of Parapox virus strain D1701 or NZ2. In further embodiments the polypeptide has a an amino acid sequence of SEQ ID NO: 2, SEQ ID NO: 4, or SEQ ID NO: 6. In still yet a further embodiments the polypeptide is a B2WL polypeptide or a PP30 polypeptide.

In preferred embodiments, introducing the polypeptide into the subject comprises introducing a nucleic acid encoding the polypeptide into the subject. In specific embodiments, the nucleic acid encodes the polypeptide of Parapox virus strain D1701 or NZ2. In still yet a further embodiment, the nucleic acid encoding the polypeptide, has a nucleic acid sequence of SEQ ID NO: 1, SEQ ID NO. 3, or SEQ ID NO: 5. In another embodiment the nucleic acid encoding the polypeptide, is a nucleic acid encoding a B2WL or a PP30 polypeptide.

Additionally, the present invention provides a nucleic acid comprised in an expression vector. In some embodiments, the expression vector is a linear or circular expression element, a plasmid vector, or a viral vector. The invention further contemplates the administration of the nucleic acid orally, by inhalation, or by injection into the subject. Further, the nucleic acid is injected via microprojectile bombardment.

In providing a method of stimulating the immune system of a subject, comprising introducing an immunostimulatory polypeptide from Parapox virus into the subject, the present invention further provides a method of stimulating, initiating or enhancing an innate immune response in the subject. In further embodiments, the immunostimulatory polypeptide is employed as an adjuvant to initiate stimulate, or enhance an immune response to a second polypeptide against which an immune response is desired. The invention further contemplates introducing a second polypeptide into the subject. In still yet another embodiment, the invention provides a method of introducing the second polypeptide into the subject comprising introducing a nucleic acid encoding the second polypeptide into the subject. The invention further embodies a method of genetic immunization, and a method of producing antibodies against the second polypeptide.

The nucleic acid encoding the second polypeptide against which an immune response is desired is comprised in a vector which further comprises a nucleic acid encoding the polypeptide adjuvant. The invention embodies a vector such as a linear or circular expression element, a plasmid vector, or a viral vector.

The invention embodies a method of genetic immunization further comprising enhancing an immune response in the subject such as a mammal. In another embodiment a mammal is a human or a mouse.

A method of genetic immunization comprising introducing into the subject a nucleic acid segment encoding a Parapox immunostimulatory polypeptide and a nucleic acid segment encoding a second polypeptide against which an immune response is desired is provided in the present invention. The protein expressed from the polypeptide is an immunostimulatory polypeptide having an amino acid sequence of SEQ ID NO: 2, SEQ ID NO: 4, or SEQ ID NO: 6, and the nucleic acid segment having a sequence of SEQ ID NO: 1, SEQ ID NO: 3, or SEQ ID NO: 5. The protein expressed from the polypeptide is a B2WL or PP30 polypeptide further defined as an immunostimulant.

The nucleic acid segment encoding the polypeptide adjuvant is comprised in a vector such as a linear or circular expression element, a plasmid vector or a viral vector. The invention further contemplates administering a nucleic acid segment encoding the polypeptide adjuvant orally, by inhalation, or by injection. The nucleic acid segment encoding the polypeptide adjuvant is injected via microprojectile bombardment.

The nucleic acid segment encoding the second polypeptide is comprised in a vector which further comprises the nucleic acid segment encoding the immunostimulatory polypeptide. The vector of the present invention further embodies a linear or circular expression element, a plasmid vector or a viral vector. The vector comprising the second polypeptide is administered orally, by inhalation, or by injection into the subject. The vector comprising the second polypeptide is injected via microprojectile bombardment.

The invention further provides a subject such as a mammal which is further defined as a human or a mouse. In a general embodiment the invention further comprising immunizing the subject.

In a particular embodiment the invention provides a construct comprising a nucleic acid encoding a Parapox immunostimulatory polypeptide such as a polypeptide of Parapox strain D1701 or NZ2. In a particular embodiment, the construct has a sequence of SEQ ID NO: 2, SEQ ID NO: 4, or SEQ ID NO: 6, and the nucleic acid sequence of SEQ ID NO: 1, SEQ ID NO: 3 or SEQ ID NO: 5. In yet another particular embodiment, the Parapox immunostimulatory polypeptide is a B2WL or PP30 polypeptide.

The construct is further defined as encoding a second polypeptide against which an immune response is desired.

In a particular embodiment the construct is further defined as a vector. The construct is further defined as a linear or circular expression element, as a plasmid vector, or as a viral vector.

In a particular embodiment the invention provides a method of initiating dendritic cell accumulation with an immunostimulatory polypeptide from parapox virus, at the site of inoculation. This method is further defined as a method for treating a subject and as a method for in vitro purification.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

The present invention relates to polypeptides that are useful in modulating immune responses and nucleic acid sequences that encode such polypeptides. A major advantage of the present invention as compared to the current approaches was realized by using the sequence of the genome and a novel expression strategy to identify genes with dendritic cell recruitment activity. The novel expression strategy-LEE-(linear expression element) was previously detailed by the inventors (U.S. patent application Ser. No: 09/535,366) as incorporated herein. The other key aspect of the invention determines that the genes identified induce dendritic cell accumulation when expressed in the skin. Furthermore, when the identified gene is co-expressed with an antigen encoding plasmid, it functions as an adjuvant stimulating antibody response to those antigens.

I. The Present Invention

The present invention utilizes the sequence of a genome and a novel expression strategy to test for genes having dendritic cell recruitment activity. In particular, the present invention employs the parapox genome and a novel expression strategy.

The present invention focuses on the biology of skin dendritic cells as regulators of immune responses. The investigators 1) determined the nature of the factor or factors derived from parapox that recruit dendritic cells to the site of infection, and 2) determined the effect of dendritic cell recruitment on generation of a specific immune response. Using a recently determined sequence of the parapox genome the inventors synthesized oligonucleotide primers and amplified open reading frame segment using PCR. Those of ordinary skill in the art will be able to determine such a parapox genome, or the genome of other organisms of use by employing methods known to them. Rather than clone each PCR product individually prior to in vivo testing, the Linear Expression Element (LEE) technology developed by the applicants (U.S. patent application Ser. No. 09/535,366) was employed as incorporated herein by reference.

The specific studies conducted are discussed in detail in the Examples below. Briefly, small pools of PCR products to which promoters and terminators were non-covalently attached were screened for biological activity (Sykes et al., 1999). This lead to the identification of a pool containing functional genes involved in recruiting dendritic cells to the site if injection. The gene identified was designated as B2WL. The effect of this immunostimulatory peptide in generating an immune response was further assessed by administration of LEEs encoding the immunostimulatory peptide which enhanced the generation of an antibody response in comparison to a known genetic adjuvant such as a plasmid encoding GM-CSF. The efficacy of B2WL as an adjuvant was further assessed by cloning this immunostimulatory peptide into a mammalian vector. B2WL was further tested on antibody responses to multiple antigens and was demonstrated to enhance these antibody responses. In the presence of an infectious pathogen such as influenza virus, the immunostimulatory peptide proved to enhance protection further demonstrating the efficacy as an adjuvant for genetic immunization. The gene designated as PP30 was identified in a separate screen testing for adjuvant activity in enhancing antibody responses to test antigens. In additional testing the adjuvant activity of PP30 proved to be more restrictive than B2WL.

Therefore, the inventors have shown how to employ inventive technologies to determine polypeptides having immunostimulatory activity and nucleic acids encoding such polypeptides. In some specific embodiments, this invention provides the sequences of three genes from parapox that are useful as immunostimulatory agents in a variety of applications, including as adjuvants to enhance the immune response induced by gene vaccines.

II. Nucleic Acids Encoding Immunostimulatory Polypeptides

The present invention identifies novel genes encoding peptides that have immunostimulatory activity. More specifically, the present invention identifies novel parapox nucleic acid sequences encoding peptides, B2WL and PP30, that have such activity. SEQ ID NO: 1 and SEQ ID NO: 3 are the B2WL sequences from D1701 and NZ2, respectively, with the respective amino acid sequences provided in SEQ. ID NO. 2 and SEQ. ID. NO. 4. Further, SEQ ID NO: 5 and SEQ ID NO: 6 contain, respectively, the nucleic acid and amino acid sequences of PP30. These genes were identified using PCR generated open reading frame (ORF) sequences to screen the parapox genome using a novel strategy incorporated by the linear expression element (LEE) technology.

Accordingly, in certain exemplary aspects, the present invention concerns nucleic acid sequences that encode proteins, polypeptides or peptides that are expressed in dendritic cell recruitment and/or adjuvant activity. In the present invention, examples of such nucleic acid sequences are the parapox genes B2WL and PP30.

The nucleic acid may be derived from genomic DNA, i.e., cloned directly from the genome of a particular organism. A nucleic acid generally refers to at least one molecule or strand of DNA, RNA or a derivative or mimic thereof, comprising at least one nucleobase, such as, for example, a naturally occurring purine or pyrimidine base found in DNA (e.g., adenine "A," guanine "G," thymine "T," and cytosine "C") or RNA (e.g. A, G, uracil "U," and C). The term nucleic acid encompasses the terms oligonucleotide and polynucleotide. The term oligonucleotide refers to at least one molecule of between about 3 and about 100 nucleobases in length. The term polynucleotide refers to at least one molecule of greater than about 100 nucleobases in length. These definitions generally refer to at least one single-stranded molecule, but in specific embodiments will also encompass at least one additional strand that is partially, substantially or fully complementary to the at least one single-stranded molecule. Thus, a nucleic acid may encompass at least one double-stranded molecule or at least one triple-stranded molecule that comprises one or more complementary strand (s) or "complement(s)" of a particular sequence comprising a strand of the molecule.

As used in this application, the term a nucleic acid encoding a immunostimulatory peptides, refers to a nucleic acid molecule that has been isolated free of total genomic nucleic acid. In preferred embodiments, the invention concerns a nucleic acid sequence essentially as set forth in SEQ ID NO: 1, SEQ ID NO: 3, or SEQ ID NO: 5. The term as set forth in SEQ ID NO: 1, SEQ ID NO: 3, or SEQ ID NO: 5 means that the nucleic acid sequence substantially corresponds to a portion or all of SEQ ID NO: 1, SEQ ID NO: 3, or SEQ ID NO: 5.

It also is contemplated that a given nucleic acid sequence such as B2WL or PP30 may be represented by natural variants that have slightly different nucleic acid sequences but, nonetheless, encode the same protein (Table 1). Furthermore, the term functionally equivalent codon is used herein to refer to codons that encode the same amino acid, such as the six codons for arginine or serine (Table 1), and also refers to codons that encode biologically equivalent amino acids, as discussed herein.

Figure 1A:
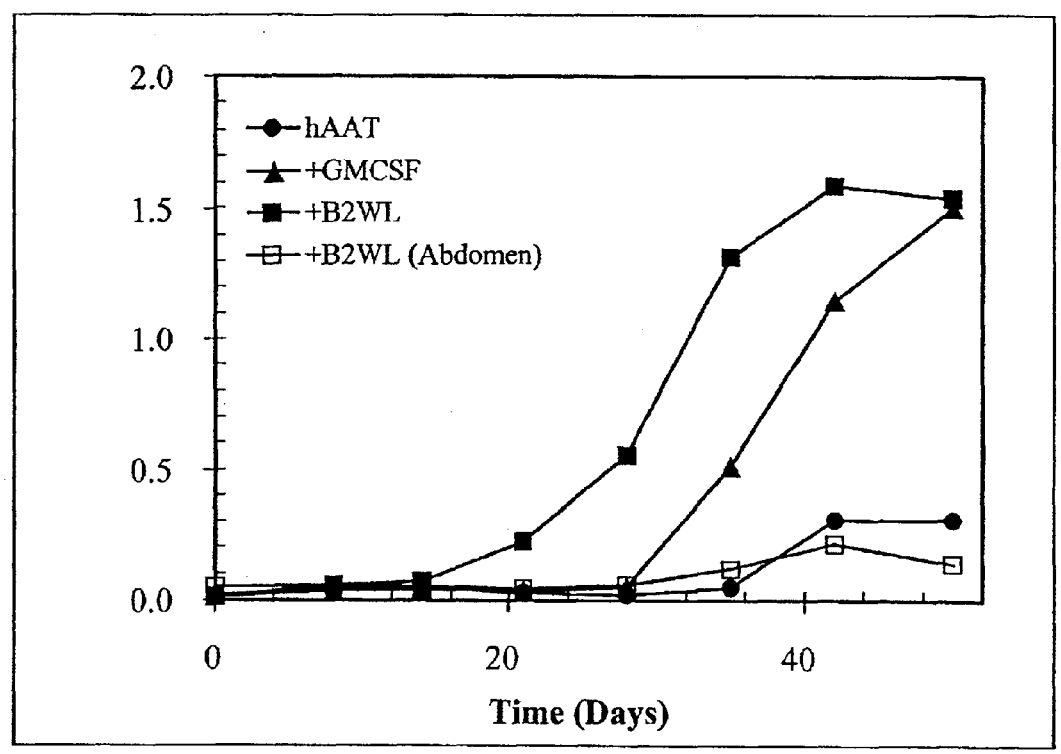
FIGS. 1A–1B. B2WL acts as a genetic adjuvant in stimulating an antibody response to hAAT.

As used herein, the term DNA segment refers to a DNA molecule that has been isolated free of total genomic DNA of a particular species. Therefore, a DNA segment encoding a polypeptide refers to a DNA segment that contains the polypeptide-coding sequences yet is isolated away from, total parapox genomic DNA. Included within the term "DNA segment" are a polypeptide or polypeptides, DNA segments smaller than a polypeptide, and recombinant vectors, including, for example, plasmids, cosmids, phage, viruses, and the like.

A DNA segment comprising an isolated immunostimulatory peptide refers to a DNA segment including immunostimulatory peptide B2WL or PP30 or other similar gene coding sequences and, in certain aspects, regulatory sequences, isolated substantially away from other naturally occurring genes or protein encoding sequences. In this respect, the term gene is used for simplicity to refer to a functional protein, polypeptide or peptide encoding unit. As will be understood by those in the art, this functional term includes both genomic sequences, cDNA sequences and smaller engineered gene segments that express, or may be adapted to express, proteins, polypeptides or peptides.

In other embodiments, the invention concerns isolated DNA segments and recombinant vectors incorporating DNA sequences that encode a polypeptide or peptide that includes within its amino acid sequence a contiguous amino acid sequence in accordance with, or essentially corresponding to the polypeptide.

It is contemplated that the nucleic acid constructs of the present invention may encode full-length polypeptide from any source. A nucleic acid sequence may encode a full-length polypeptide sequence with additional heterologous coding sequences, for example to allow for purification of the polypeptide, transport, secretion, post-translational modification, or for therapeutic benefits such as targeting or efficacy. A tag or other heterologous polypeptide may be added to the modified polypeptide-encoding sequence, wherein heterologous refers to a polypeptide that is not the same as the modified polypeptide.

In a non-limiting example, one or more nucleic acid constructs may be prepared that include a contiguous stretch of nucleotides identical to or complementary to the a particular gene, such as the B2WL and PP30 genes (SEQ ID NO: 1, SEQ ID NO: 3, SEQ ID NO: 5). A nucleic acid construct may be at least 20, 30, 40, 50, 60, 70, 80, 90, 100, 110, 120, 130, 140, 150, 160, 170, 180, 190, 200, 250, 300, 400, 500, 600, 700, 800, 900, 1,000, 2,000, 3,000, 4,000, 5,000, 6,000, 7,000, 8,000, 9,000, 10,000, 15,000, 20,000, 30,000, 50,000, 100,000, 250,000, 500,000, 750,000, to at least 1,000,000 nucleotides in length, as well as constructs of greater size, up to and including chromosomal sizes (including all intermediate lengths and intermediate ranges), given the advent of nucleic acids constructs such as a yeast artificial chromosome are known to those of ordinary skill in the art. It will be readily understood that intermediate lengths and intermediate ranges, as used herein, means any length or range including or between the quoted values (i.e., all integers including and between such values).

The DNA segments used in the present invention encompass biologically functional equivalent modified polypeptides and peptides. Such sequences may arise as a consequence of codon redundancy and functional equivalency that are known to occur naturally within nucleic acid sequences and the proteins thus encoded. Alternatively, functionally equivalent proteins or peptides may be created via the application of recombinant DNA technology, in which changes in the protein structure may be engineered, based on considerations of the properties of the amino acids being exchanged. Changes designed by human may be introduced through the application of site-directed mutagenesis techniques, e.g., to introduce improvements to the antigenicity of the protein, to reduce toxicity effects of the protein in vivo to a subject given the protein, or to increase the efficacy of any treatment involving the protein.

In addition to their use in directing the expression of the adjuvant peptides in generating an immune response of the present invention, the nucleic acid sequences contemplated herein also have a variety of other uses. For example, they also have utility as probes or primers in nucleic acid hybridization embodiments. As such, it is contemplated that nucleic acid segments that comprise a sequence region that consists of at least a 14 nucleotide long contiguous sequence that has the same sequence as, or is complementary to, a 14 nucleotide long contiguous DNA segment will find particular utility. Longer contiguous identical or complementary sequences, e.g., those of about 20, 30, 40, 50, 100, 200, 500, 1000 (including all intermediate lengths) and even up to full length sequences will also be of use in certain embodiments.

The ability of such nucleic acid probes to specifically hybridize to peptide-encoding sequences will enable them to be of use in detecting the presence of complementary sequences in a given sample. However, other uses are envisioned, including the use of the sequence information for the preparation of mutant species primers, or primers for use in preparing other genetic constructions.

TABLE 1

| Amino Acids | | | Codons |
|---|---|---|---|
| Alanine | Ala | A | GCA GCC GCG GCU |
| Cysteine | Cys | C | UGC UGU |
| Aspartic acid | Asp | D | GAC GAU |
| Glutamic acid | Glu | E | GAA GAG |
| Phenylalanine | Phe | F | UUC UUU |
| Glycine | Gly | G | GGA GGC GGG GGU |
| Histidine | His | H | CAC CAU |
| Isoleucine | Ile | I | AUA AUC AUU |
| Lysine | Lys | K | AAA AAG |
| Leucine | Leu | L | UUA UUG CUA CUC CUG CUU |
| Methionine | Met | M | AUG |
| Asparagine | Asn | N | AAC AAU |
| Proline | Pro | P | CCA CCC CCG CCU |
| Glutamine | Gln | Q | CAA CAG |
| Arginine | Arg | R | AGA AGG CGA CGC CGG CGU |
| Serine | Ser | S | AGC AGU UCA UCC UCG UCU |
| Threonine | Thr | T | ACA ACC ACG ACU |
| Valine | Val | V | GUA GUC GUG GUU |
| Tryptophan | Trp | W | UGG |
| Tyrosine | Tyr | Y | UAC UAU |

Allowing for the degeneracy of the genetic code, sequences that have at least about 50%, usually at least about 60%, more usually about 70%, most usually about 80%, preferably at least about 90% and most preferably about 95% of nucleotides that are identical to the nucleotides of SEQ ID NO: 1, SEQ ID NO: 3, and SEQ ID NO: 5 will be sequences that are as set forth in SEQ ID NO: 1, SEQ ID NO: 3, and SEQ ID NO: 5. Sequences that are essentially the same as those set forth in SEQ ID NO: 1, SEQ ID NO: 3, and SEQ ID NO: 5 also may be functionally defined as sequences that are capable of hybridizing to a nucleic acid segment containing the complement of SEQ ID NO: 1, SEQ ID NO: 3, and SEQ ID NO: 5 under standard conditions.

The DNA segments of the present invention include those encoding biologically functional equivalent B2WL and PP30 proteins and peptides, as described above. Such sequences may arise as a consequence of codon redundancy and amino acid functional equivalency that are known to occur naturally within nucleic acid sequences and the proteins thus encoded. Alternatively, functionally equivalent proteins or peptides may be created via the application of recombinant DNA technology, in which changes in the protein structure may be engineered, based on considerations of the properties of the amino acids being exchanged. Changes designed by man may be introduced through the application of site-directed mutagenesis techniques or may be introduced randomly and screened later for the desired function, as described herein.

It will also be understood that nucleic acid sequences (and their encoded amino acid sequences) may include additional residues, such as additional 5' or 3' sequences (or N- or C-terminal amino acids), and yet still be essentially as set forth in one of the sequences disclosed herein, so long as the sequence meets the criteria set forth above, including the maintenance of biological protein activity where protein expression is concerned. The addition of terminal sequences particularly applies to nucleic acid sequences that may, for example, include various non-coding sequences flanking either of the 5' or 3' portions of the coding region or may include various internal sequences, i.e., introns, which are known to occur within genes.

Excepting intronic or flanking regions of any related gene, and allowing for the degeneracy of the genetic code, sequences that have between about 70% and about 80%; or more preferably, between about 81% and about 90%; or even more preferably, between about 91% and about 99% of nucleotides that are identical to the nucleotides of a disclosed sequence are thus sequences that are essentially as set forth in the given sequence.

Immunostimulatory Polypeptides

Nucleic acids of the present invention further encodes polypeptide adjuvants as provided herein by SEQ ID NO: 2, SEQ ID NO: 4, and SEQ ID NO: 6. Amino acid sequence variants of the polypeptides of the present invention can be substitutional, insertional or deletion variants. Deletion variants lack one or more residues of the native protein that are not essential for function or immunogenic activity, and are exemplified by the variants lacking a transmembrane sequence. Another common type of deletion variant is one lacking secretory signal sequences or signal sequences directing a protein to bind to a particular part of a cell. Insertional mutants typically involve the addition of material at a non-terminal point in the polypeptide. This may include the insertion of an immunoreactive epitope or simply a single residue.

Substitutional variants typically contain the exchange of one amino acid for another at one or more sites within the protein, and may be designed to modulate one or more properties of the polypeptide, such as stability against proteolytic cleavage, without the loss of other functions or properties. Substitutions of this kind preferably are conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine.

The term biologically functional equivalent is well understood in the art and is further defined in detail herein. Accordingly, sequences that have between about 70% and about 80%; or more preferably, between about 81% and about 90%; or even more preferably, between about 91% and about 99%; of amino acids that are identical or functionally equivalent to the amino acids of a B2WL and PP30 polypeptide provided the biological activity of the protein is maintained.

The term functionally equivalent codon is used herein to refer to codons that encode the same amino acid, such as the six codons for arginine or serine, and also refers to codons that encode biologically equivalent amino acids (Table 1).

It also will be understood that amino acid and nucleic acid sequences may include additional residues, such as additional N- or C-terminal amino acids or 5' or 3' sequences, and yet still be essentially as set forth in one of the sequences disclosed herein, so long as the sequence meets the criteria set forth above, including the maintenance of biological protein activity where protein expression is concerned. The addition of terminal sequences particularly applies to nucleic acid sequences that may, for example, include various non-coding sequences flanking either of the 5' or 3' portions of the coding region or may include various internal sequences, i.e., introns, which are known to occur within genes.

The following is a discussion based upon changing of the amino acids of a protein to create an equivalent, or even an improved, second-generation molecule. For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid substitutions can be made in a protein sequence, and in its underlying DNA coding sequence, and nevertheless produce a protein with like properties. It is thus contemplated by the inventors that various changes may be made in the DNA sequences of genes without appreciable loss of their biological utility or activity, as discussed below. Table 1 shows the codons that encode particular amino acids.

In making such changes, the hydropathic index of amino acids may be considered. The importance of the hydropathic amino acid index in conferring interactive biologic function on a protein is generally understood in the art (Kyte & Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

It also is understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2) glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

It is understood that an amino acid can be substituted for another having a similar hydrophilicity value and still produce a biologically equivalent and immunologically equivalent protein. In such changes, the substitution of amino acids whose hydrophilicity values are within ±2 is preferred, those that are within ±1 are particularly preferred, and those within ±0.5 are even more particularly preferred.

As outlined herein, amino acid substitutions generally are based on the relative similarity of the amino acid side-chain substituents, for example, their hydrophobicity, hydrophilicity, charge, size, and the like. Exemplary substitutions that take into consideration the various foregoing characteristics are well known to those of skill in the art and include: arginine and lysine; glutamate and aspartate; serine and threonine; glutamine and asparagine; and valine, leucine and isoleucine.

Another embodiment for the preparation of polypeptides according to the invention is the use of peptide mimetics. Mimetics are peptide-containing molecules that mimic elements of protein secondary structure (Johnson 1993). The underlying rationale behind the use of peptide mimetics is that the peptide backbone of proteins exists chiefly to orient amino acid side chains in such a way as to facilitate molecular interactions, such as those of antibody and antigen. A peptide mimetic is expected to permit molecular interactions similar to the natural molecule. These principles may be used, in conjunction with the principles outline above, to engineer second generation molecules having many of the natural properties of adjuvants with altered and improved characteristics.

III. Delivery of Nucleic Acids Encoding Polypeptides

Vectors have long been used to deliver nucleic acids to cells, these include viral vectors and non-viral vectors. As by methods described herein and as known to the skilled artisan, expression vectors in the present invention can be constructed to deliver nucleic acids encoding an immunostimulatory peptide to a cell, tissue, or an organism. These same methods are also useful to deliver nucleic acids encoding additional polypeptides to a cell, tissue, or organism For example, in the genetic immunization aspects of the invention, when a nucleic acid encoding an immunostimulatory peptide of the invention is being used as an adjuvant in conjunction with a nucleic acid encoding a polypeptide against which an immune response is desired, both nucleic acids may be administered in one or more vectors. In this case, the adjuvant nucleic acid and antigen encoding nucleic acid may be comprised on the same vector, or they may be comprised in separate vectors.

A vector in the context of the present invention refers to a carrier nucleic acid molecule into which a nucleic acid sequence encoding a polypeptide adjuvant can be inserted for introduction into a cell and thereby replicated. A nucleic acid sequence can be exogenous, which means that it is foreign to the cell into which the vector is being introduced; or that the sequence is homologous to a sequence in the cell but positioned within the host cell nucleic acid in which the sequence is ordinarily not found. Vectors include plasmids; cosmids; viruses such as bacteriophage, animal viruses, and plant viruses; and artificial chromosomes (e.g., YACs); and synthetic vectors such as linear/circular expression elements (LEE/CEE). One of skill in the art would be well equipped to construct a vector through standard recombinant techniques as described in Sambrook et al., 2000, Maniatis et al., 1990 and Ausubel et al., 1994, incorporated herein by reference.

An expression vector refers to any type of genetic construct comprising a nucleic acid coding for a RNA capable of being transcribed. In some cases, RNA molecules are then translated into a protein, polypeptide, or peptide. In other cases, these sequences are not translated, as in the case of antisense molecules or ribozymes production. Expression vectors can contain a variety of control sequences, which refer to nucleic acid sequences necessary for the transcription and possibly translation of an operably linked coding sequence in a particular host cell. In addition to control sequences that govern transcription and translation, vectors and expression vectors may contain nucleic acid sequences that serve other functions as well, and are described herein Viral Vectors There are a number of ways in which expression vectors may be introduced into cells. In certain embodiments of the invention, the expression vector comprises a virus or engineered vector derived from a viral genome. The ability of certain viruses to enter cells via receptor-mediated endocytosis, to integrate into host cell genome and express viral genes stably and efficiently have made them attractive candidates for the transfer of foreign genes into mammalian cells (Ridgeway, 1988; Nicolas and Rubenstein, 1988; Baichwal and Sugden, 1986; Temin, 1986). The first viruses used as gene vectors were DNA viruses including the papovaviruses (simian virus 40, bovine papilloma virus, and polyoma) (Ridgeway, 1988; Baichwal and Sugden, 1986) and adenoviruses (Ridgeway, 1988; Baichwal and Sugden, 1986). These have a relatively low capacity for foreign DNA sequences and have a restricted host spectrum. Furthermore, their oncogenic potential and cytopathic effects in permissive cells raise safety concerns. They can accommodate only up to 8 kb of foreign genetic material but can be readily introduced in a variety of cell lines and laboratory animals (Nicolas and Rubenstein, 1988; Temin, 1986).

The retroviruses are a group of single-stranded RNA viruses characterized by an ability to convert their RNA to double-stranded DNA in infected cells; they can also be used as vectors. Other viral vectors may be employed as expression constructs in the present invention. Vectors derived from viruses such as vaccinia virus (Ridgeway, 1988; Baichwal and Sugden, 1986; Coupar et al., 1988) adeno-associated virus (AAV) (Ridgeway, 1988; Baichwal and Sugden, 1986; Hermonat and Muzycska, 1984) and herpesviruses may be employed. They offer several attractive features for various mammalian cells (Friedmann, 1989; Ridgeway, 1988; Baichwal and Sugden, 1986; Coupar et al., 1988; Horwich et al., 1990).

Other viral vectors may be employed as immunostimulatory peptide constructs in the present invention. Vectors derived from viruses such as vaccinia virus (Ridgeway, 1988; Baichwal and Sugden, 1986; Coupar et al., 1988), sindbis virus, cytomegalovirus and herpes simplex virus may be employed. They offer several attractive features for various mammalian cells (Friedmann, 1989; Ridgeway, 1988; Baichwal and Sugden, 1986; Coupar et al., 1988; Horwich et al., 1990).

Linear and Circular Expression Elements

Linear or circular expression elements (LEEs/CEEs) technology allows for a rapid and effective means by which to determine the activity of a particular gene product or its physiological responses, by circumventing the use of plasmids and bacterial cloning procedures. In certain embodiments, the promoter and terminator sequences of the LEE/CEE may be regarded as a type of vector.

LEEs and/or CEEs may be made according to the disclosures of U.S. patent application Ser. No.: 09/535,366, by Kathryn F. Sykes et al. filed Mar. 24, 2000, which, at the time of filing of the instant specification has been allowed but not issued. The full disclosure of U.S. patent application Ser. No.: 09/535,366, and all related applications to it is incorporated into this specification by reference.

Production of a LEE or circular expression element (CEE) generally comprise obtaining a nucleic acid segment comprising an open reading frame (ORF), and linking the ORF to a promoter, and a terminator, and/or other molecules such as a nucleic acid, to create LEE or CEE. The nucleic acid segment, terminator and/or additional nucleic acid(s) may be obtained by any method described herein or as would be known to one of ordinary skill in the art, including by nucleic acid amplification or chemical synthesis of nucleic acids such as described in EP 266,032, incorporated herein by reference, or as described by Froehler et al., 1986, and U.S. Pat. No. 5,705,629, each incorporated herein by reference. In the present invention a PCR product which comprises an ORF segment encoding a nucleic acid of B2WL or PP30 parapox genes in the presence of a promoter, a terminator, and uracil-deglycosidase (UDG), was employed in the generation of LEEs.

IV. Methods Of Delivery Of Nucleic Acids Encoding Immunostimulatory Polypeptides and/or Antigen Polypeptides Suitable methods for delivery of nucleic acid encoding an immunostimulatory peptide for transformation of a cell, tissue, or organism for use with the current invention are believed to include virtually any method by which nucleic acids can be introduced into a cell, or an organism, as described herein or as would be known to one of ordinary skill in the art. Such methods include, but are not limited to: direct delivery of DNA by injection (U.S. Pat. Nos. 5,994,624, 5,981,274, 5,945,100, 5,780,448, 5,736,524, 5,702,932, 5,656,610, 5,589,466 and 5,580,859, each incorporated herein by reference), including microinjection (Harlan and Weintraub, 1985; U.S. Pat. No. 5,789,215, incorporated herein by reference); by electroporation (U.S. Pat. No. 5,384,253, incorporated herein by reference; Tur-Kaspa et al., 1986; Potter et al., 1984); by calcium phosphate precipitation (Graham and Van Der Eb, 1973; Chen and Okayama, 1987; Rippe et al., 1990); by using DEAE-dextran followed by polyethylene glycol (Gopal, 1985); by direct sonic loading (Fechheimer et al., 1987); by liposome mediated transfection (Nicolau and Sene, 1982; Fraley et al., 1979; Nicolau et al., 1987; Wong et al., 1980; Kaneda et al, 1989; Kato et al., 1991) and receptor-mediated transfection (Wu and Wu, 1987; Wu and Wu, 1988); by microprojectile bombardment (PCT Application Nos. WO 94/09699 and 95/06128; U.S. Pat. Nos. 5,610,042; 5,322,783 5,563,055, 5,550,318, 5,538,877 and 5,538,880, and each incorporated herein by reference); by agitation with silicon carbide fibers (Kaeppler et al., 1990; U.S. Pat. Nos. 5,302,523 and 5,464,765, each incorporated herein by reference); by Agrobacterium-mediated transformation (U.S. Pat. Nos. 5,591,616 and 5,563,055, each incorporated herein by reference); or by PEG-mediated transformation of protoplasts (Omirulleh et al., 1993; U.S. Pat. Nos. 4,684,611 and 4,952,500, each incorporated herein by reference); by desiccation/inhibition-mediated DNA uptake (Potrykus et al., 1985), and any combination of such methods. Through the application of techniques such as these, organelle(s), cell(s), tissue(s) or organism(s) may be stably or transiently transformed. In certain embodiments, acceleration methods are preferred and include, for example, microprojectile bombardment.

V. Use of Immunostimulatory Polypeptides as Adjuvants in Genetic Immunization

The technology for using DNA segments as vaccines has been developed and is generally termed "Genetic Immunization" or "DNA Vaccination" (Cohen, 1993). It is now known that cells can take up naked DNA and express the peptides encoded on their surface, thus stimulating an effective immune response, which includes the generation of cytotoxic T lymphocytes (killer T cells). This technology, is particularly suitable to protect against parasites, bacteria, viral, and other pathogens.

The present invention contemplates that nucleic acids encoding immunostimulatory polypeptides my be used in conjunction with nucleic acids encoding antigenic sequences from pathogens. In the context of the present invention genetic immunization comprises introducing a nucleic acid encoding a immunostimulatory peptide into an organism, in conjunction with the introduction of an antigenic polypeptide or nucleic acid encoding an antigenic polypeptide.

For a nucleic acid encoding a immunostimulatory peptide to be useful in genetic immunization, it must enhance an immune response to the antigen in a subject (e.g., a human, or mouse). As used herein, an antigenic composition, may comprise an antigen (e.g., a peptide or polypeptide), a nucleic acid encoding an antigen (e.g., an antigen expression vector), or a cell expressing or presenting an antigen. In particular embodiments the antigenic composition comprises or encodes all or part of the sequence shown in SEQ ID NO: 1, SEQ ID NO: 3, or SEQ ID NO:: 5 or an immunologically functional equivalent thereof In other embodiments, the antigenic composition is in a mixture that comprises an additional immunostimulatory agent or nucleic acids encoding such an agent. Immunostimulatory agents include but are not limited to an additional antigen, an immunomodulator, an antigen presenting cell or an adjuvant. In other embodiments, one or more of the additional agent(s) is covalently bonded to the antigen or an immunostimulatory agent, in any combination. In certain embodiments, the antigenic composition is conjugated to or comprises an HLA anchor motif amino acids. Antigens may be identified by genome-wide searches for novel useful sequences using the ELI strategy or by bio-informatic screens. Alternatively, adjuvants may be used to obtain immune responses to characterized genes which have failed to induce desired antibody responses in previous trials.

Enhancing an Immune Response Adjuvants

The primary purpose of an adjuvant is to enhance the immune response to a particular antigen of interest. In the present invention enhancement of an immune response is mediated by a nucleic acid encoding a immunostimulatory peptide which increases the humoral response to an antigen. The present invention provides a method of such enhancement of an immune response in a mammalian subject such as a human or mouse, by contacting said subject with a nucleic acid encoding a immunostimulatory peptide or a immunostimulatory peptide directly.

As known to the skilled artisan, selection of an adjuvant is based upon antigen characteristics such as size, net charge, and the presence or absence of polar groups. Adjuvant choice is also dependent upon selection of the species to be immunized. Adjuvants may also be selected by comparing antibody response after immunization with antigen complexed to different adjuvants.

Adjuvants may act through three basic mechanisms. The first is to enhance long term release of the antigen by functioning as a depot. An antigen may aid in the immune response by forming a depot of antigen at the injection site resulting in the sustained release of small quantities of antigen over a long period of time. Long term exposure to the antigen should increase the length of time the immune system is presented with the antigen for processing as well as the duration of the antibody response. The second mechanism is the interaction the adjuvant has with immune cells. Adjuvants may act as non-specific mediators of immune cell function by directly or indirectly stimulating or modulating immune cells. Thirdly, adjuvants may also serve as a vehicle to deliver the antigen to the spleen and/or lymph nodes where antigen is trapped by the follicular dendritic cells and where most of the necessary cell to cell interactions take place to generate plasma cells. Adjuvants may also enhance macrophage phagocytosis after binding the antigen as a particulate (a carrier/vehicle function).

One group of adjuvants of practical use in the present invention are those that can be encoded by nucleic acids. It is contemplated that such adjuvants may be encoded in a LEE or CEE vector encoding the antigen, or as separate LEE or CEE vectors, or traditional plasmids or other constructs. These nucleic acid encoding the immunostimulatory peptide can be delivered directly, such as for example with lipids or liposomes. In other embodiments, the present invention utilizes the use of open reading frames (ORFs) which encode a nucleic acid encoding a immunostimulatory peptide which are further employed in making LEEs. An open reading frame comprises a series of tri-nucleotides that encode one or more amino acids. ORFs isolated from an organism may encode an endogenous peptide, polypeptide, protein or non-translated mRNA message. In the present invention both DNA strands in all possible reading frames, not excluding overlapping reading frames, were searched.

Immunization protocols have used adjuvants to stimulate responses for many years. Some adjuvants affect the way in which antigens are presented. For example, the immune response is increased when protein antigens are precipitated by alum. Emulsification of antigens also prolongs the duration of antigen presentation. Other adjuvants, for example, certain organic molecules obtained from bacteria, act on the host rather than on the antigen. An example is muramyl dipeptide (N-acetylmuramyl-L-alanyl-D-isoglutamine [MDP]), a bacterial peptidoglycan. The effects of MDP, as with most adjuvants, are not fully understood. MDP stimulates macrophages but also appears to stimulate B cells directly. The effects of adjuvants, therefore, are not antigen-specific. If they are administered together with a purified antigen, however, they can be used to selectively promote the response to the antigen.

VI. Antibody Production and Uses Thereof

In the present invention, genetic adjuvants such as a plasmid encoding a protein or a LEE/CEE encoding a nucleic acid enhance the generation of an antibody response These antibodies may further be utilized in diagnostic and therapeutic applications.

Means for preparing and characterizing antibodies are well known in the art (e.g., Antibodies: A Laboratory Manual, Cold Spring Harbor Laboratory, 1988; incorporated herein by reference). As used herein, the term antibody is intended to refer broadly to any immunologic binding agent such as IgG, IgM, IgA, IgD and IgE. Generally, IgG and/or IgM are preferred because they are the most common antibodies in the physiological situation and because they are most easily made in a laboratory setting.

The term antibody is used to refer to any antibody-like molecule that has an antigen binding region, and includes antibody fragments such as Fab', Fab, F(ab')$_2$, single domain antibodies (DABs), Fv, scFv (single chain Fv), and the like. The techniques for preparing and using various antibody-based constructs and fragments are well known in the art. Means for preparing and characterizing antibodies are also well known in the art (See, e.g., Antibodies: A Laboratory Manual, Cold Spring Harbor Laboratory, 1988; incorporated herein by reference).

Monoclonal antibodies (MAbs) are recognized to have certain advantages, e.g., reproducibility and large-scale production, and their use is generally preferred. MAbs may be readily prepared through use of well-known techniques, such as those exemplified in U.S. Pat. No. 4,196,265, incorporated herein by reference.

VII. Pharmacological Preparations of Nucleic Acids and Polypeptides Routes of Delivery/Administration The preparation of vaccines which contain peptides or nucleic acids encoding peptides as active ingredients is generally well understood in the art, as exemplified by U.S. Pat. Nos. 4,608,251; 4,601,903; 4,599,231; 4,599,230; 4,596,792; and 4.578,770, all incorporated herein by reference. Typically, such vaccines are prepared as injectables, either as liquid solutions or suspensions or solid forms suitable for solution in, or suspension in, liquid prior to injection. The preparation may also be emulsified. The active immunogenic ingredient is often mixed with excipients which are pharmaceutically acceptable and compatible with the active ingredient. Suitable excipients are, for example, water, saline, dextrose, glycerol, ethanol, or the like and combinations thereof. In addition, if desired, the vaccine may contain minor amounts of auxiliary substances such as wetting or emulsifying agents, pH buffering agents, or adjuvants which enhance the effectiveness of the vaccines.

Vaccines may be conventionally administered parenterally, by injection, for example, either subcutaneously or intramuscularly.

The manner of application may be varied widely. Any of the conventional methods for administration of a vaccine are applicable. These are believed to include gene gun inoculation of the DNA encoding the antigen peptide(s), phage transfection of the DNA, oral application on a solid physiologically acceptable base or in a physiologically acceptable dispersion, parenterally, by injection or the like. The dosage of the vaccine will depend on the route of administration and will vary according to the size of the host.

Various methods of achieving adjuvant effect for the vaccine includes use of agents such as aluminum hydroxide or phosphate (alum), commonly used as about 0.05 to about 0.1% solution in phosphate buffered saline, admixture with synthetic polymers of sugars (Carbopol®) used as an about 0.25% solution, aggregation of the protein in the vaccine by heat treatment with temperatures ranging between about 70° to about 101° C. for a 30-second to 2-minute period, respectively. Aggregation by reactivating with pepsin treated (Fab) antibodies to albumin, mixture with bacterial cells such as *C. parvm* or endotoxins or lipopolysaccharide components of Gram-negative bacteria, emulsion in physiologically acceptable oil vehicles such as mannide mono-oleate (Aracel A) or emulsion with a 20% solution of a perfluorocarbon (Fluosol-DA®) used as a block substitute may also be employed.

Administration of Nucleic Acids

One method for the delivery of a nucleic acid encoding a immunostimulatory peptide and/or antigenic peptide as in the present invention is via gene gun injection. As known to the skilled artisan, the two main methods of administration of DNA vaccines are via particle bombardment, achieved using a gene gun, or via intramuscular saline injection. For the gene gun method as employed by the present invention, the DNA is coated onto gold particles which are then fired into the target tissue which is usually the epidermis. Gene gun methods have been shown to be the most efficient as the same level of antibody and cellular immunity may be gained using 100–5000 fold less DNA than is necessary for injection methods (Pertmer et al., 1995; Fynan et al., 1993). Although the gene gun method is more efficient it has not been shown to have longer lived responses or provide better protection from pathogenic challenge than intramuscular vaccination (Cohen et al., 1998). The interesting difference between the two methods is that they elicit different Th responses. The intramuscular inoculation is associated with a Th-1 response producing elevated interferon gamma, little IL-4 and more IgG2a than IgG1 antibodies (Pertmer et al., 1996). The gene gun method, on the other hand, produces a Th-2 response, on successive immunizations, with the opposite cytokine and antibody profile to the intramuscular inoculation. However, the pharmaceutical compositions disclosed herein may alternatively be administered parenterally, intravenously, intradermally, intramuscularly, transdermally or even intraperitoneally as described in U.S. Pat. No. 5,543,158; U.S. Pat. No. 5,641,515 and U.S. Pat. No. 5,399,363 (each specifically incorporated herein by reference in its entirety).

Injection of a nucleic acid encoding a immunostimulatory peptide and/or antigen may be delivered by syringe or any other method used for injection of a solution, as long as the expression construct can pass through the particular gauge of needle required for injection. A novel needleless injection system has recently been described (U.S. Pat. No. 5,846,233) having a nozzle defining an ampule chamber for holding the solution and an energy device for pushing the solution out of the nozzle to the site of delivery. A syringe system has also been described for use in gene therapy that permits multiple injections of predetermined quantities of a solution precisely at any depth (U.S. Pat. No. 5,846,225).

Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms. The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, intratumoral and intraperitoneal administration. In this connection, sterile aqueous media that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion, (for example, "Remington's Pharmaceutical Sciences"15th Edition, pages 1035–1038 and 1570–1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The compositions disclosed herein may be formulated in a neutral or salt form. Pharmaceutically-acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug release capsules and the like.

As used herein, carrier includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The phrase "pharmaceutically-acceptable" or "pharmacologically-acceptable" refers to molecular entities and compositions that do not produce an allergic or similar untoward reaction when administered to a human. The preparation of an aqueous composition that contains a protein as an active ingredient is well understood in the art. Typically, such compositions are prepared as injectables, either as liquid solutions or suspensions; solid forms suitable for solution in, or suspension in, liquid prior to injection can also be prepared.

A vaccination schedule and dosages may be varied on a subject by subject basis, taking into account, for example, factors such as the weight and age of the subject, the type of disease being treated, the severity of the disease condition, previous or concurrent therapeutic interventions, the manner of administration and the like, which can be readily determined by one of ordinary skill in the art.

A vaccine is administered in a manner compatible with the dosage formulation, and in such amount as will be therapeutically effective and immunogenic. For example, the intramuscular route may be preferred in the case of toxins with short half lives in vivo. The quantity to be administered depends on the subject to be treated, including, e.g., the capacity of the individual's immune system to synthesize antibodies, and the degree of protection desired. The dosage of the vaccine will depend on the route of administration and will vary according to the size of the host. Precise amounts of an active ingredient required to be administered depend on the judgment of the practitioner. In certain embodiments, pharmaceutical compositions may comprise, for example, at least about 0.1% of an active compound. In other embodiments, the an active compound may comprise between about 2% to about 75% of the weight of the unit, or between about 25% to about 60%, for example, and any range derivable therein However, a suitable dosage range may be, for example, of the order of several hundred micrograms active ingredient per vaccination. In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per vaccination, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above. A suitable regime for initial administration and booster administrations (e.g., inoculations) are also variable, but are typified by an initial administration followed by subsequent inoculation(s) or other administration(s).

In many instances, it will be desirable to have multiple administrations of the vaccine, usually not exceeding six vaccinations, more usually not exceeding four vaccinations and preferably one or more, usually at least about three vaccinations. The vaccinations will normally be at from two to twelve week intervals, more usually from three to five week intervals. Periodic boosters at intervals of 1–5 years, usually three years, will be desirable to maintain protective levels of the antibodies.

The course of the immunization may be followed by assays for antibodies for the supernatant antigens. The assays may be performed by labeling with conventional labels, such as radionuclides, enzymes, fluorescents, and the like. These techniques are well known and may be found in a wide variety of patents, such as U.S. Pat. Nos. 3,791,932; 4,174,384 and 3,949,064, as illustrative of these types of assays. Other immune assays can be performed and assays of protection from challenge with the immunostimulatory peptide can be performed, following immunization.

VIII. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice.

All of the compositions and methods disclosed and claimed herein can be made and executed without undue experimentation in light of the present disclosure. While the compositions and methods of this invention are described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

Example 1

Materials and Methods Relating to Studies with Parapox Strain D1701

Parapox virus (D1701 strain) was obtained from Tobias Schlapp of Bayer Pharmaceuticals, Germany. Female BALB/c and A/J mice were purchased from Harlan Laboratories (Indianapolis, Ind.) Oligonucleotide primers for PCR generation of individual open reading frame segments (orfs) were synthesized using either an ABI synthesizer or the MerMade3 high throughput synthesizer. The parapox directed oligonucleotides were designed with distinct dU-containing flanks that allowed the PCR products to be annealed to compatible dU-flanked CMV promoter and hGH terminator PCR products. FITC-conjugated rat anti-I-$A^d$/I-$E^d$ antibody (2G9), rat anti-I-$A^k$ antibody (11-5.2) and unlabelled rat anti-CD16/CD32 (Fc block, 2.4G2) were purchased from Pharmingen (San Diego, Calif.). Rat IgG was purchased from Jackson Laboratories (West Grove, Pa.). Tissue Freezing Medium (Triangle Biomedical Sciences, Durham, N.C.) and Superfrost Plus microscope slides were obtained from Fisher Chemical Co (Norcross, Ga.). Vectashield fluorescence microscopy mounting medium was obtained from Vector Laboratories (Burlingame, Calif.).

Example 2

PCR Amplification of Parapox Genes

The sequence of the 150 kb parapox genome, which was determined by the inventors was searched for ORFs using the Mac Vector sequence analysis program. The parameters were set such that each ORF included start and stop codons and encoded a protein with a minimum length of 90 amino acids. The search included both strands, in all possible reading frames and did not exclude overlapping reading frames. This search yielded 288 possible ORFs. In addition, 3 full-length protein-coding sequences from the NZ-2 strain of the ORF parapox virus were present in the NCBI sequence database. These sequences were similar to, but not identical with, sequences the inventors had determined. Therefore, to be most inclusive, specific primers to each of these 291 possible ORFs were synthesized and used to generate individual PCR products for testing. Each primer set contained dU-flanking sequences that allowed for the directional annealing of the CMV-promoter fragment to the 5' end of the orf and the hGH terminator fragment to the 3' end of the orf. 257 of the predicted PCR products were successfully obtained (88%). 34 products were not obtained, even after resynthesizing primers and modifying PCR conditions. These orfs were excluded from additional analysis. PCR products were obtained using the following conditions. Each 50 µl reaction contained 10 pmol of forward and reverse primer, 5 ng parapox genomic DNA template, 10 mM Tris-HCl, pH 8.8, 50 mM potassium glutamate, 0.1% Triton X-100, 2 mM $MgCl_2$, 0.2 mM dNTP, 1M betaine and 2.5 U Taq polymerase. Each reaction was overlaid with mineral oil and incubated according to the following parameters in a Stratagene Robocycler. An initial cycle consisted of 3 min denaturation at 95° C., 1 min annealing at 55° C. and 1 min extension at 72° C. This was followed by 10 cycles of 1 min denaturation at 94° C., 1 min annealing at 55° C. and 1 min extension at 72° C. and 24 cycles of 1 min at 94° C., 1 min at 50° C. and 1 min at 72° C. The PCR was finished with a 5 minute extension at 72° C. All PCR products were assessed by electrophoresis in 1.2% agarose gels and DNA concentration was determined using a Hoeffer fluorometer and Hoechst dye and plasmid DNA as standard.

Example 3

Preparation of Linear Expression Elements (LEEs)

PCR products (400 ng each) were pooled in groups of 8–10 and purified from primers, etc., using Qiaquick spin columns per supplied protocols (Qiagen, Inc., Valencia, Calif.). DNA pools were eluted from the columns in 50 µl 10 mM Tris-HCl, pH 8.5. 1 µg DNA from each PCR pool was mixed with CMV promoter PCR product and hGH terminator PCR product and 0.5 unit uracil-deglycosidase in a final volume of 50 µl 1× Buffer C (Promega Corp., Madison, Wis.). The samples were incubated at 37° C. for at least 30 min, heated to 75° C. for 15 min and mixed with an equal volume of 1 M KCl. After incubating an additional 15 min at 72° C., the components were allowed to anneal by slowly cooling to room temperature. The LEEs were precipitated by the addition of sodium acetate and ethanol. The precipitated DNA was collected by centrifugation and washed with 70% ethanol and allowed to dry before it was resuspended in water and loaded on gold for biolistic inoculation into skin.

Example 4

Gene Gun Inoculation and Skin Sampling

The desired amount of total DNA was precipitated onto gold beads. The DNA-gold complexes were then spotted onto kapton membranes and dried. The complexes were introduced into mouse abdominal skin that had been prepared by treatment with shears and Nair depilatory. Each mouse was treated with 4–6 shots of the DNA-gold complexes. The recruitment of dendritic cells to the site of inoculation was assessed after 4 days. To assess the dendritic cell recruitment, the mice were euthanized, the location of the inoculations marked and the abdominal skin was harvested. Inoculation sites were isolated and trimmed of surrounding tissue. Skin segments were immersed in cryoprotective medium and quickly frozen in liquid nitrogen. Thin-sections (8 µm) were cut in a Leitz cryostat, picked up on Superfrost plus microscope slides and stored at −20° C. for subsequent fixation and staining.

Frozen sections were equilibrated to room temperature for 10 minutes then fixed by immersion in cold acetone for 10 minutes. The fixed sections were washed 3 times in phosphate buffered saline pH 7.3 (PBS). Non-specific adherence of rat IgG was blocked by treatment of the sections with a cocktail of Fc block reagent and rat IgG in PBS. After a 30-minute incubation at room temperature, this blocking solution was replaced by FITC-conjugated rat anti-I-$A^d$/I-$E^d$ antibody (2G9) and incubation continued for 2 hours. The sections were washed 3 times in PBS and prepared for viewing by the addition of Vectashield mounting medium and a cover slip. The stained sections were viewed under white light to locate the area of gene gun inoculation marked by the presence of gold beads. These areas were then assessed for the presence of dendritic cells (FITC-labeled, anti-I-$A^d$/I-$E^d$ antibody positive cells with dendritic morphology) under fluorescence microscopy.

Example 5

Assessment of B2WL on Antibody Induction

In order to determine the potential effect of DC recruitment as an adjuvant in generating a specific immune response, a plasmid containing the cDNA encoding human $\alpha_1$-anti-trypsin (hAAT) was inoculated into mouse skin in the presence or absence of the parapox B2WL gene. Previous experiments by the inventors have shown that BALB/c mice respond poorly to a one-time inoculation using a total of 1 µg hAAT plasmid in the absence of an adjuvant. At various times after inoculation, blood was collected from each mouse and assayed for the presence of antibodies to hAAT by ELISA. Assay plates were coated with hAAT protein in PBS(10 µg/ml; 50 µl/well) or HBsAg in PBS (10 ng/ml; 50 µl/well) overnight at 4° C. After the antigen solution was removed, plates were washed 3 times, blocked with 1% BSA in wash buffer and incubated with diluted mouse sera. The plates were washed and mouse anti-hAAT or anti-HBsAg antibodies were allowed to react with rabbit anti-mouse-Ig-HRP conjugate. Plates were washed again and developed with TMB substrate solution. HRP reactions were stopped by addition of 0.25 M HCl and absorbence at 450 nm determined for each well.

Example 6

Coding Sequences from ORF of Parapox

By PCR amplification of segments of the parapox genome, (D1701 strain), the inventors identified full-length coding sequences from ORF of parapox. Specific primers were synthesized to the ORFs (open reading frame) generating individual PCR products. Utilizing the linear expression element (LEE) technology, the 257 PCR products, generated as detailed in Methods, were grouped in sets of 8–10 for in vivo testing of DC recruiting activity. The PCR products were then purified from primers and linked to promoter and terminator elements.

Each pool consisted of 400 ng of each PCR product as well as the PCR-generated CMV promoter and terminator fragments. The pools were treated with UDG and 2 μg total DNA was precipitated on gold beads and the complexes introduced into the abdominal skin of mice by gene gun inoculation with luciferase as a control of the gene gun. Each mouse received 4–6 shots of the complexes. Each pool was screened in at least 3 mice. After 4 days, the mice were sacrificed and the sites of inoculation were processed for assessment of DC recruitment by staining for MHC class II positive cells.

Dermal dendritic cells form an intricate lattice under the epidermis of mouse skin. This lattice is observed when untreated mouse skin is stained for MHC class II bearing cells. However, when skin is bombarded with DNA-coated gold beads many of the dendritic cells leave the site of inoculation. It is thought that these cells may react to a "danger" signal and migrate to the draining lymph node to activate other cells involved in the immune response.

A skin site inoculated with a LEE encoding luciferase was used as a control to assess the effect of gene gun DNA inoculation and also compared to a section of untreated skin. Mice are not in the natural host range of the parapox virus, and therefore a control inoculation of complete virus could not be used to compare the effect of each pool of ORFs.

Eight individual ORFs were obtained from the pool designated as Pool X as described in Table 2. This set included the 3 ORFs generated from sequences obtained from the NCBI database as well as 5 sequences deduced by sequencing the parapox genome. The designations of these ORFs were: B2WL, B3L and NZ2-IL10 (NCBI database); 270, 272, 277, 278, and 279 (inventors sequence). (NZ2-B2WL is present in the NCBI database as B2L). Blast searches of the sequence databases revealed that ORF 277 was the homolog of the IL-10 present in the parapox strain (D1701). Thus, pool X contained 2 doses of homologs to the mouse IL-10 gene. Interestingly, the B3L homolog sequence did not appear in the original ORF list because the translated product contained only 89 amino acids (criteria included a 90 amino acid minimum translation product). A full length B2WL homolog from the D1701 strain was not identified in initial sequencing work due to an error in the preliminary determination of the 3' end of the gene. This error led to the prediction of a smaller ORF (truncated protein) that had been included in pool J. Pool J did not induce the accumulation of dendritic cells indicating that the truncated form of the protein was not fully functional for this activity.

TABLE 2

Components of Parapox Pool X

| ORF Designation | Size (bp) | Annotation |
| --- | --- | --- |
| B2WL | 1134 | OV p42K (Vac p37K (EEV) protein) |
| B3L | 267 | OV p10K |
| NZ2-TL10 | 540 | TL-10 homolog |
| 270 | 609 | No known homology |
| 272 | 1572 | Ankyrin-repeat |

TABLE 2-continued

Components of Parapox Pool X

| ORF Designation | Size (bp) | Annotation |
| --- | --- | --- |
| 277 | 555 | IIL-10 homolog |
| 278 | 1503 | Ankyrin-repeat |
| 279 | 312 | No known homology |

Each of these eight products were further inoculated into mice utilizing the gene gun technique either separately or in complexes. B2WL appeared to encode the protein responsible for dendritic cell recruitment activity in Pool X. Since the main goal of immunization is to provide protection against an infectious disease, adjuvants are only useful when they enhance protection of vaccinated subjects challenged with an infectious pathogen. The effect of B2WL as an adjuvant was further assessed by co-inoculation with antigen encoding plasmid such as hAAT and Hbs Ag, and found to enhance the generation of antibodies in response to these antigens. This adjuvant (B2WL) was effective in enhancing protection of animals that received a partially protective influenza vaccine. In the presence of the highest doses of the influenza vaccine administered, only animals that also received the adjuvant were fully protected. SEQ. ID. NO 1 and SEQ. ID. NO 3 represent the nucleic acid sequences of B2WL, and SEQ. ID. NO 2 and SEQ. ID. NO 4 the amino acid sequences.

Example 7

Effect of B2WL on Generation of a Humoral Immune Response

After observing that B2WL effectively recruited dendritic cells to a site of inoculation, the effect this gene would have on the generation of an immune response was assessed. Previous work by the inventors has demonstrated that the dendritic cells at the site of gene gun inoculation are the most potent initiators of an immune response. However, after immunization with the gene gun, the majority of exogenous protein is expressed in other skin cells such as keratinocytes. Thus, the consequence of accumulating dendritic cells at the site of inoculation could potentially alter the immune response in 3 radically distinct ways. By causing the dendritic cells to accumulate at the site of inoculation rather than homing to the draining lymph node, an immune response might be diminished. Alternatively, the dendritic cells at the inoculation site would have additional time to process antigens synthesized by neighboring cells before going to the lymph node and initiating an immune response. Finally, B2WL inoculation may have no effect on the generation of an immune response.

As detailed in FIG. 1A, mice were inoculated with a low dose (0.5 μgDNA/ear;1 μg total/mouse) of a plasmid encoding human $\alpha_1$-anti-trypsin (hAAT). When inoculated by itself, the low dose is below the threshold of antibody induction with a single immunization. However, when administered in the presence of a genetic adjuvant, such as a plasmid encoding GM-CSF, an antibody response to hAAT is observed in most mice. The addition of LEEs encoding B2WL enhanced the generation of an antibody response to HAAT. In fact, the animals that received the B2WL LEEs along with the hAAT antigen exhibited an earlier antibody response than the mice that received GM-CSF as adjuvant. The responses of the 2 groups were similar with respect to the levels of circulating antibodies to hAAT that were obtained without a booster inoculation. Interestingly, the adjuvant effect of B2WL was only observed when B2WL and hAAT were inoculated at the same sites on the mice. The mice inoculated with hAAT plasmid in the ear and the B2WL in the abdomen did not generate a strong antibody response.

Figure 1B:
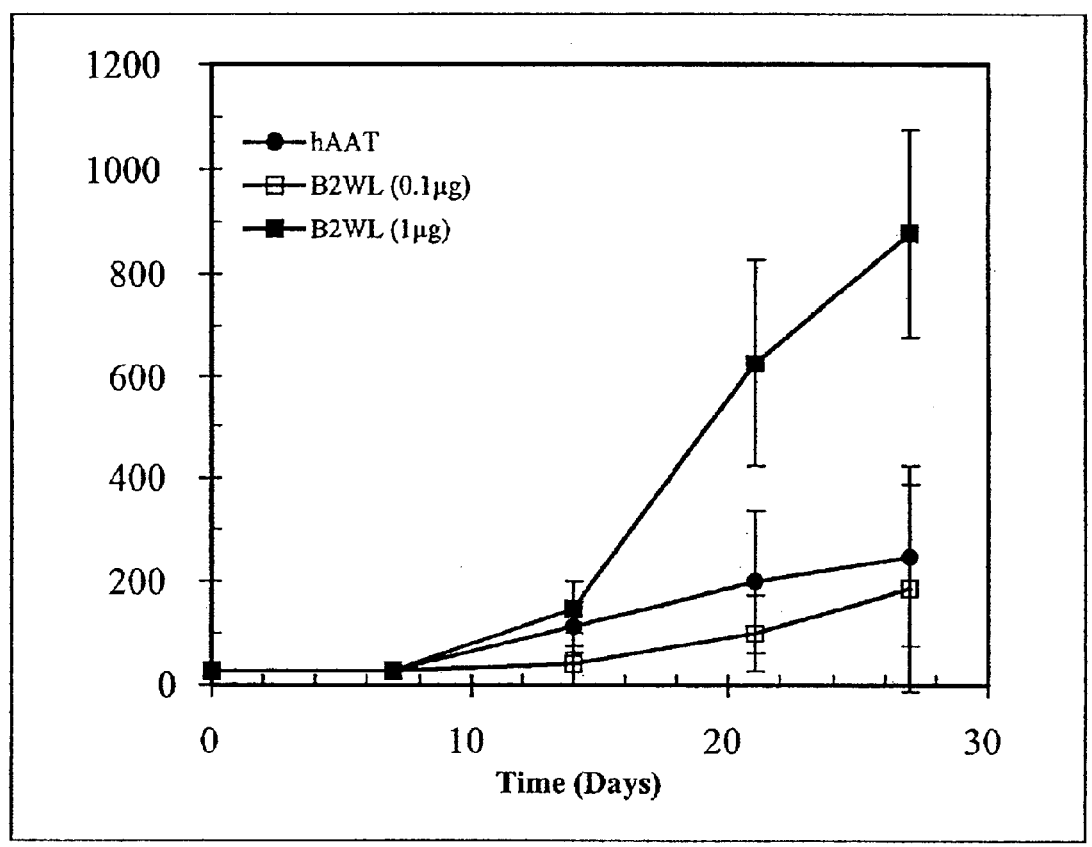

The inventors cloned the B2WL gene in a mammalian expression vector (pCMVi) and assessed the adjuvant effect at 2 dosages. As shown in FIG. 1B, the adjuvant effect of B2WL is readily demonstrated when the B2WL plasmid was administered at a dose of 1 µg/mouse. However, the adjuvant effect was lost when mice were given only 0.1 µg B2WL/mouse.

Example 8

Testing Against Multiple Antigens

Figure 2:
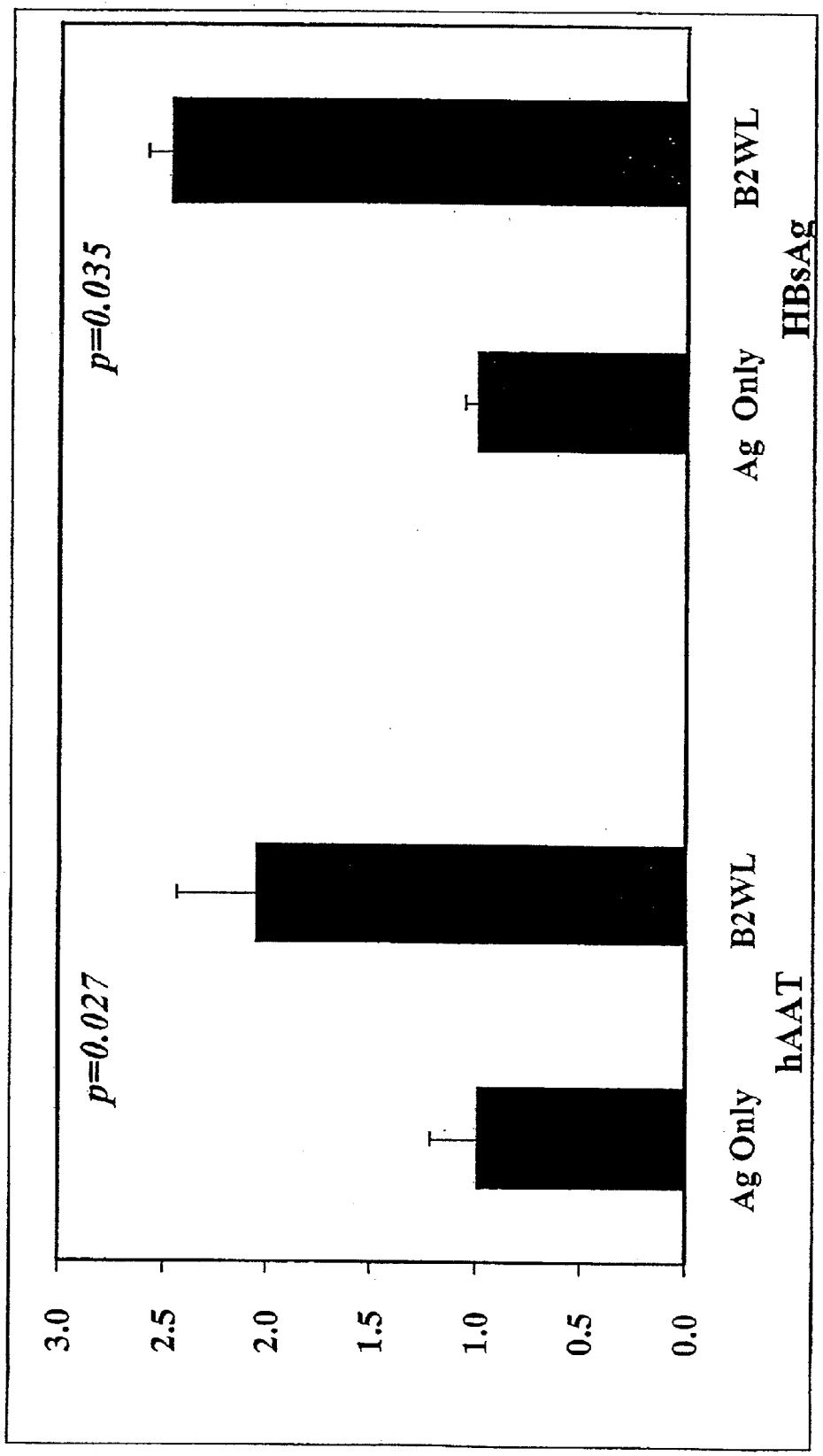
FIG. 2. B2WL stimulates antibody responses to multiple antigens.

To further assess the usefulness of B2WL as an adjuvant the inventors tested the effect of B2WL on antibody responses to multiple antigens. In these experiments, B2WL was co-inoculated with plasmids encoding hAAT and hepatitis B surface antigen (HbsAg). The level of each antigen-encoding plasmid was reduced to 0.2 µg/inoculation with B2WL or control plasmid at 1 µg/inoculation. As detailed in FIG. 2, B2WL enhanced the generation of antibodies in response to both hAAT and HbsAg.

Example 9

Testing B2WL in an Infection Challenge System

Figure 3:
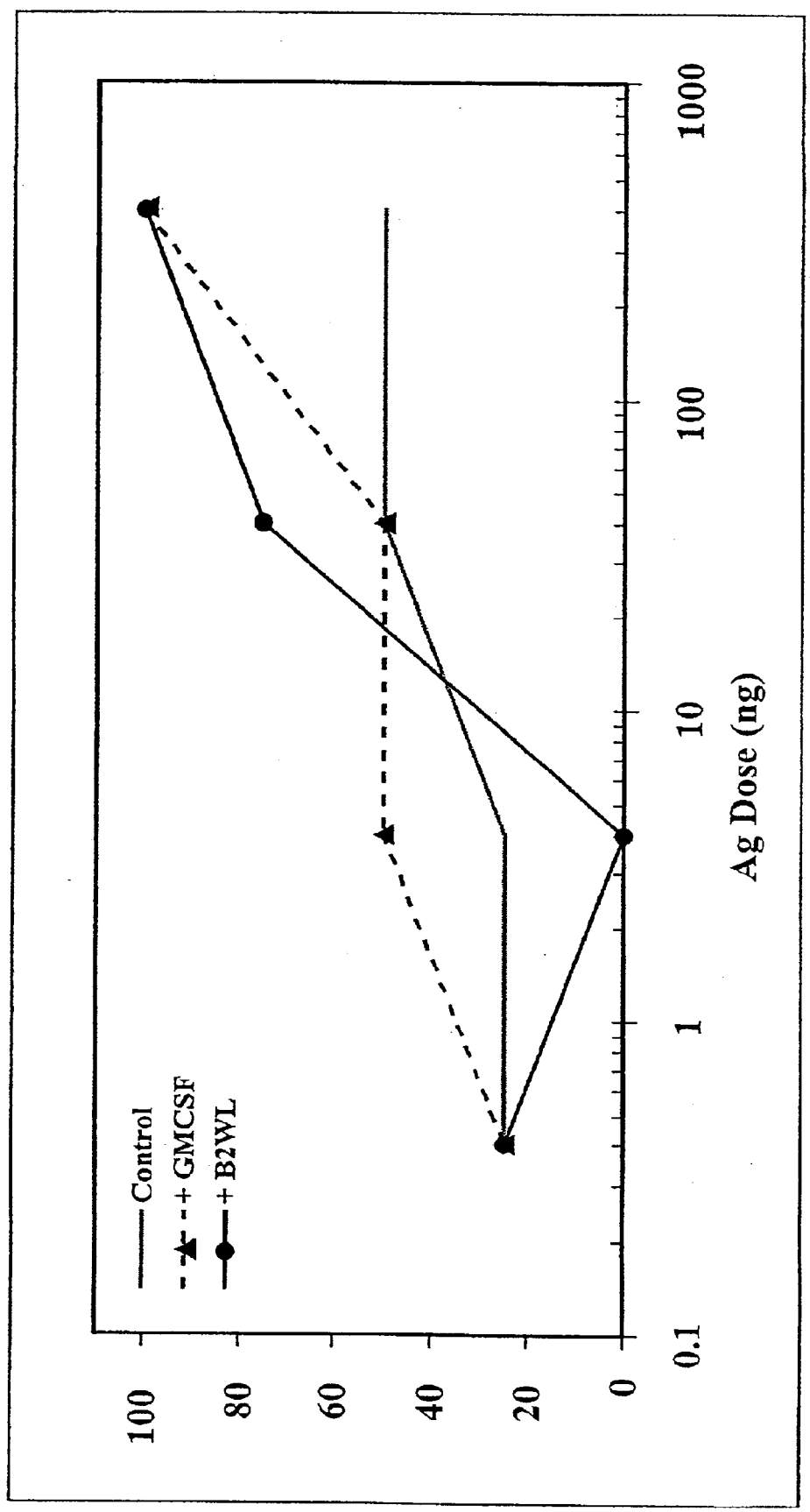
FIG. 3. B2WL enhances protective immunity to influenza.

The real goal of any immunization is to provide protection against infectious disease. An adjuvant will only be useful if it enhances a protective response in the face of the challenge with an infectious pathogen. Therefore, the effect of B2WL on the generation of a protective immune response for influenza virus. Mice were immunized twice with plasmid encoding influenza hemagglutinin (pCMVi-HA). Mice were immunized with 4 levels (0.4–400 ng) of pCMVi-HA plasmid along with 1 µg control plasmid, pCMVi-mGMCSF, or pCMVi-B2WL. When challenged with influenza virus, mice that were immunized without adjuvant still succumbed to the infection (FIG. 3). 50% of the mice that received the highest dose of antigen (400 ng/immunization) without adjuvant died upon challenge. In contrast, mice that were immunized with this antigen level in the presence of B2WL were fully protected. This level of protection was also observed with the control adjuvant, mGMCSF. In this initial experiment, B2WL also enhanced the level of protection for mice that were immunized with only 40 ng pCMVi-HA. At this level, B2WL exhibited a protective benefit compared to mGMCSF.

Example 10

Searching the Parapox Genome for Additional Immunostimulatory Polypeptides

The observation that a parapox gene identified by dendritic cell recruitment, B2WL, served as an adjuvant for genetic immunization suggested that other parapox genes might also have adjuvant activity even in the absence of dendritic cell recruitment activity. Therefore, the inventors tested all parapox genes for direct adjuvant activity by assessing their effect on antibody responses in mice inoculated with plasmid encoding hAAT. Each ORF was tested in sets of 8–10 as used for the DC recruitment assay. Each ORF was independently tested twice by arraying the genes in a 2-dimensional grid. In 2 rounds of screening for adjuvant activity a second unique parapox gene, designated PP30, was identified. SEQ ID NO: 5 and SEQ ID NO: 6 are the nucleic acid and amino acid sequences of PP30, respectively.

The adjuvant activity of PP30 appears to be more restrictive than B2WL as it stimulated the antibody response to hAAT but had little effect on response to HbsAg. PP30 is a newly identified gene with no apparent homolog in the NCBI database. The function of PP30 in parapox is unknown.

Example 11

Assessing the B2WL Gene of Parapox Strain NZ2 for Immunostimulatory Activity

Comparison of the sequences of B2WL from the D1701 strain obtained in the inventors laboratory to the related gene in the NZ2 strain (individual sequence in the NCBI database) identified sequence differences at both the nucleotide and predicted protein levels. Therefore, the inventors obtained DNA from the NZ2 strain of parapox, amplified the NZ2-B2WL gene by PCR and cloned this into pCMVi plasmid. The efficacy of NZ2-B2WL and D1701-B2WL was then compared.

Example 12

Obtaining Nucleic Acid Potentially Encoding Immunostimulatory Peptides

The invention may further employ the use of a genomic expression immunization procedure such as ELI in identifying immunostimulatory peptides. Such an expression library will incorporate potential antigenic determinants of an organism. The preparation of an expression library is performed using techniques and methods familiar to the molecular biologist.

The source of potential antigenic determinants may be bacterial, yeast, mold, fungal, algal, protozoan, or viral, and the genome of the source may or may not be known and may have been cloned. DNA (or cDNA). Nucleic acid from the source may be broken up, by physical fragmentation or restriction endonuclease, into segments of some length so as to provide a library of about $10^1$ (x genome size) members. For cloned DNA in YACs, a sufficient library may be available. In cases, where the genome is RNA, the RNA may be used to prepare a DNA library. From the prepared expression library, plasmid DNA is isolated using methods as is know to the skilled artisan and as incorporated herein. A subject such as a mouse or human may then be immunized with the entire library or a portion thereof.

Example 13

Testing Putative Immunostimulatory Peptide Encoding Sequences

Plasmid DNA isolated from an expression immunization library may be inoculated into the subject using microprojectile bombardment by employing gene gun or needle injection methods to test for immunostimulatory peptides. Any of the one of several different methods incorporated herein for delivery of nucleic acid encoding an immunostimulatory peptide, or as is known to the skilled artisan may also be employed in testing the immunostimulatory peptide. Dendritic cell migration testing, as discussed above, may be used in this regard.

Example 14

Using Determined Immunostimulatory Peptides

Immunostimulatory peptides identified using the techniques disclosed herein may be further utilized in generating an immune response.

REFERENCES

The following references, to the extent that they provide exemplary procedural or other details supplementary to those set forth herein, are specifically incorporated herein by reference.

U.S. patent application Ser. No. 09/535,366
U.S. Pat. No. 3,791,932
U.S. Pat. No. 3,949,064
U.S. Pat. No. 4,174,384
U.S. Pat. No. 4,196,265
U.S. Pat. No. 4,554,101
U.S. Pat. No. 4,578,770
U.S. Pat. No. 4,596,792
U.S. Pat. No. 4,599,230
U.S. Pat. No. 4,599,231
U.S. Pat. No. 4,601,903
U.S. Pat. No. 4,608,251
U.S. Pat. No. 4,684,611
U.S. Pat. No. 4,952,500
U.S. Pat. No. 5,302,523
U.S. Pat. No. 5,322,783
U.S. Pat. No. 5,384,253
U.S. Pat. No. 5,399,363
U.S. Pat. No. 5,464,765
U.S. Pat. No. 5,466,468
U.S. Pat. No. 5,538,877
U.S. Pat. No. 5,538,880
U.S. Pat. No. 5,543,158
U.S. Pat. No. 5,550,318
U.S. Pat. No. 5,563,055
U.S. Pat. No. 5,580,859
U.S. Pat. No. 5,589,466
U.S. Pat. No. 5,591,616
U.S. Pat. No. 5,610,042
U.S. Pat. No. 5,641,515
U.S. Pat. No. 5,656,610
U.S. Pat. No. 5,702,932
U.S. Pat. No. 5,705,629
U.S. Pat. No. 5,736,524
U.S. Pat. No. 5,780,448
U.S. Pat. No. 5,789,215
U.S. Pat. No. 5,846,225
U.S. Pat. No. 5,846,233
U.S. Pat. No. 5,945,100
U.S. Pat. No. 5,981,274
U.S. Pat. No. 5,994,624
Antibodies: A Laboratory Manual, Cold Spring Harbor Laboratory, Cold Spring Harbor Press, Cold Spring Harbor, N.Y., 1988.
Ausubel et al., In: *Current Protocols in Molecular Biology*, John, Wiley & Sons, Inc, New York, 1994.
Baichwal and Sugden, In: *Gene Transfer*, Kucherlapati (ed.), New York, Plenum Press, 117–148, 1986.
Chen and Okayama, *Mol. Cell Biol.*, 7(8):2745–2752, 1987.
Cohen, *Science*, 259(5102): 1691–1692, 1993.
Cohen, *FASEB J*, 12(15):1611–26, 1998.
Coupar et al., *Gene*, 68:1–10, 1988.
Diven, *J Am Acad Dermatol*, 44(1): 1–16, 2001.
European Patent No. EP 266,032
Fechheimer et al., *Proc. Nat'l Acad. Sci. USA*, 84:8463–8467, 1987.
Fraley et al., *Proc. Nat'l Acad. Sci. USA*, 76:3348–3352, 1979.
Friedmann, *Science*, 244:1275–1281, 1989.
Froehler et al., *Nucleic Acids Res.* 14(13):5399–5407, 1986.
Fynan et al., *Proc. Natl. Acad. Sci. USA*, 90:11478–11482, 1993.
Gopal, *Mol. Cell Biol.*, 5:1188–1190, 1985.
Graham and Van Der Eb, *Virology*, 52:456–467, 1973.
Harland and Weintraub, *J. Cell Biol.*, 101:1094–1099, 1985.
Hermonat and Muzyczka, *Proc. Nat'l. Acad. Sci. USA*, 81:6466–6470, 1984.
Horwich et al. *J. Virol.*, 64:642–650, 1990.
Johannessen J V, et al., *J. Cutan. Pathol.* 2:265–283, 1975.
Johnson et al., In: *Biotechnology And Pharmacy*, Pezzuto et al., eds., Chapman and Hall, New York, 1993.
Kaeppler et al., *Plant Cell Reports* 9:415–418, 1990.
Kaneda et al., *Science*, 243:375–378, 1989.
Kato et al, *J. Biol. Chem.*, 266:3361–3364, 1991.
Kyte and Doolittle, *J. Mol. Biol.*, 157(1):105–132, 1982.
Maniatis, et al., Molecular Cloning, A Laboratory Manual, Cold Spring Harbor Press, Cold Spring Harbor, N.Y., 1990.
McKeever D J, et al., *J. Comp. Path.* 99:317–328, 1988.
Nicolas and Rubenstein, In: *Vectors: A survey of molecular cloning vectors and their uses*, Rodriguez and Denhardt (eds.), Stoneham: Butterworth, pp. 493–513, 1988.
Nicolau and Sene, *Biochim. Biophys. Acta*, 721:185–190, 1982.
Nicolau et al., *Methods Enzymol.*, 149:157–176, 1987.
Omirulleh et al., *Plant Mol. Biol.*, 21(3):415–28, 1993.
PCT Application No. WO 94/09699
PCT Application No. WO 95/06128
Pertmer et al., *J Virol*, 70(9):6119–25, 1996.
Pertmer et al., *Vaccine*, 13(15):1427–30, 1995.
Potrykus et al., *Mol. Gen. Genet.*, 199(2):169–77, 1985.
Potter et al., *Proc. Nat'l Acad. Sci. USA*, 81:7161–7165, 1984.
Remington's Pharmaceutical Sciences, 15$^{th}$ ed., pages 1035–1038 and 1570–1580, Mack Publishing Company, Easton, Pa., 1980.
Ridgeway, In: *Vectors: A survey of molecular cloning vectors and their uses*, Stoneham: Butterworth, pp. 467–492, 1988.
Rippe et al., *Mol. Cell Biol.*, 10:689–695, 1990.
Sambrook et al., In: *Molecular cloning*, Cold Spring Harbor Laboratory Press, Cold Spring Harbor, N.Y., 2000.
Sjolander et al., *Mol Immunol*, 35(3):159–66, 1998.
Sykes, K F and S A Johnston L., *Nature Biotechnology* 17:355–359, 1999.
Temin, In: *Gene Transfer*, Kucherlapati (ed.), New York: Plenum Press, pp. 149–188, 1986.
Tur-Kaspa et al., *Mol. Cell Biol.*, 6:716–718, 1986.
Wong et al., *Gene*, 10:87–94, 1980.
Wu and Wu, *Biochemistry*, 27:887–892, 1988.
Wu and Wu, *J. Biol. Chem.*, 262:4429–4432, 1987.
Yin et al., *J. Biological Response Modifiers*, 8:190–205, 1989.

What is claimed is:

1. A method of initiating or enhancing an immune response of a subject to an antigen, the method comprising administering to the subject (a) the antigen or a nucleic acid encoding the antigen, and (b) a B2L or pp30 protein of a parapox virus, or a nucleic acid encoding said protein, wherein said protein or nucleic acid is unassociated with other components naturally associated with the protein or nucleic acid in the virus.

2. The method of claim 1, wherein the protein is of Parapox virus strain D1701 or NZ2.

3. The method of claim 1, wherein the protein comprises SEQ ID NO:2, SEQ ID NO:4 or SEQ ID NO:6.

4. The method of claim 1, wherein the subject is a mammal.

5. The method of claim 1, wherein the subject is a human.

6. The method of claim 1, wherein the administering comprises introducing into the subject a nucleic acid encoding the parapox protein.

7. The method of claim 6, wherein the parapox protein encoding nucleic acid is comprised in a vector.

8. The method of claim 6, wherein the parapox protein encoding nucleic acid is administered orally, by inhalation or by injection into the subject.

9. The method of claim 6, wherein the protein is of Parapox virus strain D1701 or NZ2.

10. The method of claim 6, wherein the protein comprises SEQ ID NO:2 SEQ ID NO:4 or SEQ ID NO:6.

11. The method of claim 6, wherein the subject is a mammal.

12. The method of claim 6, wherein the subject is a human.

13. The method of claim 1, wherein the administering comprises introducing into the subject a nucleic acid encoding the antigen.

14. The method of claim 13, wherein the antigen encoding nucleic acid is comprised in a vector.

15. The method of claim 13, wherein the antigen encoding nucleic acid is administered orally, by inhalation, or by injection into the subject.

16. The method of claim 13, wherein the protein is of Parapox virus strain D1701 or NZ2.

17. The method of claim 13, wherein the protein comprises SEQ ID NO:2, SEQ ID NO:4 or SEQ ID NO:6.

18. The method of claim 13, wherein the subject is a mammal.

19. The method of claim 13, wherein the subject is a human.

20. The method of claim 1, wherein the administering comprises introducing into the subject a nucleic acid encoding the parapox protein and a nucleic acid encoding the antigen.

21. The method of claim 20, wherein the antigen encoding nucleic acid and the parapox protein nucleic said are comprised in a vector.

22. The method of claim 20, wherein the antigen encoding nucleic acid and the parapox protein nucleic acid are administered orally, by inhalation, or by injection into the subject.

23. The method of claim 20, wherein the protein is of Parapox virus strain D1701 or NZ2.

24. The method of claim 20, wherein the protein comprises SEQ ID NO:2, SEQ ID NO:4 or SEQ ID NO:6.

25. The method of claim 20, wherein the subject is a mammal.

26. The method of claim 20, wherein the subject is a human.

* * * * *

SEQUENCE LISTING

<160> NUMBER OF SEQ ID NOS: 6

<210> SEQ ID NO 1
<211> LENGTH: 1137
<212> TYPE: DNA
<213> ORGANISM: PARAPOX

<400> SEQUENCE: 1

| | | | | | |
|---|---|---|---|---|---|
| atgtggccgt | tctcctccat | ccccgtgggc | gcccaatgcc | gcgtcttgga | aacgctgccc | 60 |
| gcagaggtgg | cgtccctggc | gcagggcaac | atgagcaccc | tcgactgctt | caccgccatc | 120 |
| gccgagtccg | cgaagaaatt | tttgtacatc | tgcagcttct | gctgcaacct | gagctccacc | 180 |
| aaggagggcg | tcgacgtcaa | agacaagctc | tgcacgctcg | ccaaggaagg | cgttgacgtc | 240 |
| acgctgctcg | tggacgtgca | gagcaaggac | aaggacgcgg | acgaactgcg | cgcggcgggc | 300 |
| gtcaactact | acaaggtcaa | agtgtccacg | cgggaaggcg | tcggcaacct | tctcggcagc | 360 |
| ttctggctct | cggacgccgg | gcactggtac | gtgggcagcg | cctcgctcac | gggcgggtcc | 420 |
| gtgtccacca | tcaagaacct | cgggctctac | tccaccaaca | agcacctggc | ctgggacctc | 480 |
| atgaaccgct | acaacaccct | ctactccatg | atcgtggagc | cgaaggtgcc | gttcacgcgg | 540 |
| ctctgctgcg | ccgtcgtcac | gcccacggcc | acgaacttcc | acctcaacca | ctccgggggc | 600 |
| ggcgtattct | tctcggactc | gccggagcgc | ttcctaggct | tctaccgcac | gctcgacgag | 660 |
| gacctcgtgc | tgcaccgcat | cgagaacgcc | aagaacagca | tcgacctctc | gctgctctcg | 720 |
| atggtgccgg | tgatcaagca | cgccggcgcc | gtggagtact | ggccgcggat | catagacgcg | 780 |
| ctgctgcgcg | cggccatcaa | ccgcggcgtg | cgcgtgcgcg | tgatcatcac | cgagtggaag | 840 |
| aacgcggacc | cgctgtcggt | ctcggccgcg | cgcagcctcg | acgactttgg | cgtcggtagc | 900 |
| gtggacatgt | ccgtgcgcaa | gttcgtggta | cccggccggg | acgacgctgc | gaacaacacc | 960 |
| aagctgctta | tcgtggacga | caccttcgcg | cacctcacgg | tcgccaacct | cgacggcacg | 1020 |
| cactaccgct | accacgcctt | cgtgagcgtg | aacgccgaga | agggcgacat | cgtcaaggac | 1080 |
| ctgtccgcgg | tcttcgagcg | ggactggcgc | tcggagtttt | gcaagccaat | aaattaa | 1137 |

<210> SEQ ID NO 2
<211> LENGTH: 378
<212> TYPE: PRT
<213> ORGANISM: PARAPOX

<400> SEQUENCE: 2

Met Trp Pro Phe Ser Ser Ile Pro Leu Gly Ala Gln Cys Arg Val Leu
 1               5

-continued

```
Gly Val Gly Asn Leu Leu Gly Ser Phe Trp Leu Ser Asp Ala Gly His
        115                 120                 125

Trp Tyr Val Gly Ser Ala Ser Leu Thr Gly Gly Ser Val Ser Thr Ile
    130                 135                 140

Lys Asn Leu Gly Leu Tyr Ser Thr Asn Lys His Leu Ala Trp Asp Leu
145                 150                 155                 160

Met Asn Arg Tyr Asn Thr Phe Tyr Ser Met Ile Val Glu Pro Lys Val
                165                 170                 175

Pro Phe Thr Arg Leu Cys Cys Ala Val Val Thr Pro Thr Ala Thr Asn
            180                 185                 190

Phe His Leu Asn His Ser Gly Gly Gly Val Phe Phe Ser Asp Ser Pro
        195                 200                 205

Glu Arg Phe Leu Gly Phe Tyr Arg Thr Leu Asp Glu Asp Leu Val Leu
    210                 215                 220

His Arg Ile Glu Asn Ala Lys Asn Ser Ile Asp Leu Ser Leu Leu Ser
225                 230                 235                 240

Met Val Pro Val Ile Lys His Ala Gly Ala Val Glu Tyr Trp Pro Arg
                245                 250                 255

Ile Ile Asp Ala Leu Leu Arg Ala Ala Ile Asn Arg Gly Val Arg Val
            260                 265                 270

Arg Val Ile Ile Thr Glu Trp Lys Asn Ala Asp Pro Leu Ser Val Ser
        275                 280                 285

Ala Ala Arg Ser Leu Asp Asp Phe Gly Val Gly Ser Val Asp Met Ser
    290                 295                 300

Val Arg Lys Phe Val Val Pro Gly Arg Asp Asp Ala Ala Asn Asn Thr
305                 310                 315                 320

Lys Leu Leu Ile Val Asp Asp Thr Phe Ala His Leu Thr Val Ala Asn
                325                 330                 335

Leu Asp Gly Thr His Tyr Arg Tyr His Ala Phe Val Ser Val Asn Ala
            340                 345                 350

Glu Lys Gly Asp Ile Val Lys Asp Leu Ser Ala Val Phe Glu Arg Asp
        355                 360                 365

Trp Arg Ser Glu Phe Cys Lys Pro Ile Asn
    370                 375
```

<210> SEQ ID NO 3
<211> LENGTH: 1137
<212> TYPE: DNA
<213> ORGANISM: PARAPOX

<400> SEQUENCE: 3

```
atgtggccgt tctcctccat ccccctgggc gccgactgcc gcgtcgtgga gacgctgccc      60
gcagaggtgg cgtctttggc gcagggcaac atgagcaccc tcgactgctt caccgctatc     120
gccgagtccg cgaagaagtt cttgtacatc tgcagcttct gctgcaacct gagctccacc     180
aaggagggcg tcgacgtcaa ggacaagctc tgcacgctcg ccaaggaggg cgtagacgtc     240
acgctgctcg tggacgtgca gagcaaggac aaggacgcgg acgagctgcg cgaggcgggc     300
gtcaactact acaaggtcaa ggtgtccacc aaggagggcg tcggcaacct tctcggcagc     360
ttctggctct cggacgccgg gcactggtac gtgggaagcg cctcgctcac gggcgggtcc     420
gtgtccacca tcaagaacct cgggctctac tccaccaaca agcacctggc ctgggacctc     480
atgaaccgct acaacacctt ctactccatg atcgtggagc cgaaggtgcc gttcacgcgg     540
ctctgctgcg ccatcgtcac gcccacggcc acgaacttcc acctcgacca ctccgggggc     600
```

-continued

```
ggcgtattct tctcggactc gccggagcgc ttcctaggct tctaccgcac gctcgacgag    660
gacctcgtgc tgcaccgcat cgagaacgcc aagaacagca tcgacctctc gctgctctcg    720
atggtgccgg tgatcaagca cgccagcgcc gtggagtact ggccgcagat cattgacgcg    780
ctgctgcgcg cggccatcaa ccgcggcgtg cgcgtgcgcg tgatcattac cgagtggaag    840
aacgcggacc cgctttcggt ctcggccgcg cgcagcctcg acgactttgg cgtcggcagc    900
gtggacatgt ccgtgcgcaa gttcgtggta cccggccggg acgacgccgc gaacaacact    960
aagctgctca tcgtggacga caccttcgcg cacctcacgg tcgccaacct cgacggcacg   1020
cactaccgct accacgcctt cgtgagcgtg aacgccgaga agggcgacat cgtcaaggac   1080
ctgtccgcgg tcttcgagcg ggactggcgc tcggagttct gcaagccaat aaattaa     1137
```

<210> SEQ ID NO 4
<211> LENGTH: 378
<212> TYPE: PRT
<213> ORGANISM: PARAPOX

<400> SEQUENCE: 4

```
Met Trp Pro Phe Ser Ser Ile Pro Leu Gly Ala Asp Cys Arg Val Val
  1               5                  10                  15

Glu Thr Leu Pro Ala Glu Val Ala Ser Leu Ala Gln Gly Asn Met Ser
             20                  25                  30

Thr Leu Asp Cys Phe Thr Ala Ile Ala Glu Ser Ala Lys Lys Phe Leu
         35                  40                  45

Tyr Ile Cys Ser Phe Cys Cys Asn Leu Ser Ser Thr Lys Glu Gly Val
     50                  55                  60

Asp Val Lys Asp Lys Leu Cys Thr Leu Ala Lys Glu Gly Val Asp Val
 65                  70                  75                  80

Thr Leu Leu Val Asp Val Gln Ser Lys Asp Lys Asp Ala Asp Glu Leu
                 85                  90                  95

Arg Glu Ala Gly Val Asn Tyr Tyr Lys Val Lys Val Ser Thr Lys Glu
            100                 105                 110

Gly Val Gly Asn Leu Leu Gly Ser Phe Trp Leu Ser Asp Ala Gly His
        115                 120                 125

Trp Tyr Val Gly Ser Ala Ser Leu Thr Gly Gly Ser Val Ser Thr Ile
    130                 135                 140

Lys Asn Leu Gly Leu Tyr Ser Thr Asn Lys His Leu Ala Trp Asp Leu
145                 150                 155                 160

Met Asn Arg Tyr Asn Thr Phe Tyr Ser Met Ile Val Glu Pro Lys Val
                165                 170                 175

Pro Phe Thr Arg Leu Cys Cys Ala Ile Val Thr Pro Thr Ala Thr Asn
            180                 185                 190

Phe His Leu Asp His Ser Gly Gly Val Phe Phe Ser Asp Ser Pro
        195                 200                 205

Glu Arg Phe Leu Gly Phe Tyr Arg Thr Leu Asp Glu Asp Leu Val Leu
    210                 215                 220

His Arg Ile Glu Asn Ala Lys Asn Ser Ile Asp Leu Ser Leu Leu Ser
225                 230                 235                 240

Met Val Pro Val Ile Lys His Ala Ser Ala Val Glu Tyr Trp Pro Gln
                245                 250                 255

Ile Ile Asp Ala Leu Leu Arg Ala Ala Ile Asn Arg Gly Val Arg Val
            260                 265                 270

Arg Val Ile Ile Thr Glu Trp Lys Asn Ala Asp Pro Leu Ser Val Ser
```

```
              275                 280                 285
Ala Ala Arg Ser Leu Asp Asp Phe Gly Val Gly Ser Val Asp Met Ser
        290                 295                 300

Val Arg Lys Phe Val Val Pro Gly Arg Asp Ala Ala Asn Asn Thr
305                 310                 315                 320

Lys Leu Leu Ile Val Asp Asp Thr Phe Ala His Leu Thr Val Ala Asn
                325                 330                 335

Leu Asp Gly Thr His Tyr Arg Tyr His Ala Phe Val Ser Val Asn Ala
            340                 345                 350

Glu Lys Gly Asp Ile Val Lys Asp Leu Ser Ala Val Phe Glu Arg Asp
            355                 360                 365

Trp Arg Ser Glu Phe Cys Lys Pro Ile Asn
370                 375

<210> SEQ ID NO 5
<211> LENGTH: 408
<212> TYPE: DNA
<213> ORGANISM: PARAPOX

<400> SEQUENCE: 5
atggacgcgg tgtccgcgct ctgcgtgagc cctcgcggca gccgccgcca tgttcgtggc      60
gctgcagctc tgggccgtct acgagaacta cgacaacatc cgcgagttca cgcggcgaa     120 cgcggcgctg gagttcgcgc gcacggcggg cggcccgcgc gtggaccggc gcgtgttcga    180
ccccaacgac gaggccttcg acgtgcgcaa gaagtggcgc tgcgtgctct tcaagggcgc    240
ggcggtggcg gcctcggagt tcgggtttcg ttcgcacgac ggcgtctcgc ccgcgcgctt    300
cgcgagcgtg ggaggcgtgt gcggacgaga tcttcacggc cgcgagcgac ttccgcgtgt    360 tcaaccgtg tttgccgcca aatcagggca gcgaggcctg cctttttc                  408

<210> SEQ ID NO 6
<211> LENGTH: 136
<212> TYPE: PRT
<213> ORGANISM: PARAPOX

<400> SEQUENCE: 6

Met Asp Ala Val Ser Ala Leu Cys Val Ser Pro Arg Gly Ser Arg Arg
  1               5                  10                  15

His Val Arg Gly Ala Ala Ala Leu Gly Arg Leu Arg Glu Leu Arg Gln
             20                  25                  30

His Pro Arg Val Gln Arg Gly Glu Arg Gly Ala Gly Val Arg Ala His
         35                  40                  45

Gly Gly Arg Pro Ala Arg Gly Pro Ala Arg Val Arg Pro Gln Arg Arg
     50                  55                  60

Gly Leu Arg Arg Ala Gln Glu Val Ala Leu Arg Ala Leu Gln Gly Arg
 65                  70                  75                  80

Gly Gly Gly Gly Leu Gly Val Arg Val Ser Phe Ala Arg Arg Arg Leu
                 85                  90                  95

Ala Arg Ala Leu Arg Glu Arg Gly Arg Arg Val Arg Thr Arg Ser Ser
            100                 105                 110

Arg Pro Arg Ala Thr Ser Ala Cys Ser Thr Arg Val Cys Arg Gln Ile
        115                 120                 125

Arg Ala Ala Arg Pro Ala Phe Phe
    130                 135
```